(12) United States Patent
Yalin et al.

(10) Patent No.: US 7,412,129 B2
(45) Date of Patent: Aug. 12, 2008

(54) FIBER COUPLED OPTICAL SPARK DELIVERY SYSTEM

(75) Inventors: Azer Yalin, Fort Collins, CO (US);
Bryan Willson, Fort Collins, CO (US);
Morgan Defoort, Fort Collins, CO (US)

(73) Assignee: Colorado State University Research Foundation, Ft. Collins, CO (US)

(*) Notice: Subject to any disclaimer, the term of this patent is extended or adjusted under 35 U.S.C. 154(b) by 161 days.

(21) Appl. No.: 11/126,908

(22) Filed: May 10, 2005

(65) Prior Publication Data
US 2006/0055925 A1 Mar. 16, 2006

Related U.S. Application Data

(60) Provisional application No. 60/598,932, filed on Aug. 4, 2004.

(51) Int. Cl.
*G02B 6/26* (2006.01)
(52) U.S. Cl. .......................................... 385/31; 385/33
(58) Field of Classification Search ....................... None
See application file for complete search history.

(56) References Cited

U.S. PATENT DOCUMENTS

| | | |
|---|---|---|
| 3,258,910 A | 7/1966 | Seymour |
| 4,314,530 A | 2/1982 | Giacchetti |
| 4,416,226 A | 11/1983 | Nishida et al. |
| 4,523,552 A | 6/1985 | Mukainakano et al. |
| 4,852,529 A | 8/1989 | Vowles |
| 4,917,014 A | 4/1990 | Loughry et al. |
| 5,328,665 A | 7/1994 | Geiger |
| 5,367,869 A | 11/1994 | DeFreitas |
| 5,617,717 A | 4/1997 | Asquith et al. |
| 5,673,550 A | 10/1997 | Few et al. |
| 5,983,871 A | 11/1999 | Gordon et al. |

(Continued)

FOREIGN PATENT DOCUMENTS

| | | |
|---|---|---|
| JP | 63-90643 | 4/1988 |
| JP | 63-105261 | 5/1988 |
| WO | 98/11388 | 3/1998 |

OTHER PUBLICATIONS

Gaborel, G. et al., "Toward the Development of a Laser Ignition System for Aircraft Engines." Oct. 2005, pp. 1-8.

(Continued)

*Primary Examiner*—Sung H Pak
(74) *Attorney, Agent, or Firm*—Sheridan Ross P.C.

(57) ABSTRACT

A spark delivery system for generating a spark using a laser beam is provided, the spark delivery system including a laser light source and a laser delivery assembly. The laser delivery assembly includes a hollow fiber and a launch assembly comprising launch focusing optics to input the laser beam in the hollow fiber. In addition, the laser delivery assembly includes exit focusing optics that demagnify an exit beam of laser light from the hollow fiber, thereby increasing the intensity of the laser beam and creating a spark. In accordance with embodiments of the present invention, the assembly may be used to create a spark in a combustion engine. In accordance with other embodiments of the present invention, a method of using the spark delivery system is provided. In addition, a method of choosing an appropriate fiber for creating a spark using a laser beam is also presented.

42 Claims, 6 Drawing Sheets

U.S. PATENT DOCUMENTS

| | | | |
|---|---|---|---|
| 6,053,140 | A | 4/2000 | Feichtinger et al. |
| 6,520,142 | B2 | 2/2003 | Nogi et al. |
| 6,676,402 | B1 | 1/2004 | Early et al. |
| 6,749,726 | B2 | 6/2004 | Edelman et al. |
| 6,762,835 | B2 | 7/2004 | Zhang et al. |
| 6,796,278 | B2 | 9/2004 | Ryan, III |
| 6,802,290 | B1 | 10/2004 | Wintner et al. |
| 6,898,359 | B2 | 5/2005 | Soljacic et al. |
| 6,903,357 | B2 | 6/2005 | Robb |
| 2003/0031443 | A1* | 2/2003 | Soljacic et al. .............. 385/125 |

OTHER PUBLICATIONS

Parry, J. et al., "Analysis of Optical Damage Mechanisms in Hollow Core Waveguides Delivering Nanosecond Pulses From a Q-Switched Nd:YAG Laser." Published by OSA. Doc. id 71526. Posted Aug. 2006, pp. 1-33.

International Search Report for International (PCT) Patent Application No. PCT/US05/27894, mailed Apr. 30, 2007.

Written Opinion for International (PCT) Patent Application No. PCT/US05/27894, mailed Apr. 30, 2007.

Official Action for U.S. Appl. No. 11/197,832, mailed Mar. 2, 2007.

Official Action for U.S. Appl. No. 11/197,833, mailed Jul. 24, 2007.

U.S. Appl. No. 11/197,832, filed Aug. 4, 2005, Yalin et al.

U.S. Appl. No. 11/197,833, filed Aug. 4, 2005, Yalin et al.

Lee et al.; "Laser Spark Ignition of Chemically Reactive Gases"; *AIAA Journal*; 1969; 7(2):312-317.

Ronney; "Laser Versus Conventional Ignition of Flames"; *Opt. Eng.*; Feb. 1994; 33(2):510-521.

Spiglanin et al.; "Tiime-Resolved Imaging of Flame Kernels: Laser Spark Ignition of $H_2/O_2/Ar$ Mixtures"; *Combustion and Flame*; 1995; 102:310-328.

Ma et al.; "Nd: YAG Laser Ignition of Natural Gas"; *ASME: ICE-Spring Technical Conference, Paper No. 98-ICE-114*; 1998, 30-3:117-125.

Phuoc et al.; "Laser-Induced Spark Ignition of $CH_4$/Air Mixtures"; *Combustion and Flame*; 1999; 119:203-216.

Phuoc; "Brief Communication—Single-Point Versus Multi-Point Laser Ignition: Experimental Measurements of Combustion Times and Pressures"; *Combustion and Flame*; 2000; 122:508-510.

Chen et al.; "Visualization of Laser-Induced Breakdown and Ignition"; *Opt. Exp.*; 2001; 9(7):360-372.

Kopecek et al.; "Laser Ignition of Methane-Air Mixtures at High Pressures"; *Exptl. Therm. and Fluid Sci.*; 2003; 27:499-503.

Beduneau et al.; "Measurements of Minimum Ignition Energy in Premixed Laminar Methane/Air Flow by Using Laser Induced Spark"; *Combustion and Flame*; 2003; 132:653-665.

Lackner et al.; "Investigation of the Early Stages in Laser-Induced Ignition by Schlieren Photography and Laser-Induced Fluorescence Spectroscopy"; *Opt. Exp.*, 2004; 12(19):4546-4557.

Bradley et al.; "Fundamentals of High-Energy Spark Ignition with Lasers"; *Combustion and Flame*; 2004; 138:55-77.

Kopecek et al.; "Laser Ignition of Methane-Air Mixtures at High Pressures and Diagnostics"; *Jnl. Of Eng. for Gas Turb. and Power*; 2005; 127:213-219.

Weinrotter et al.; "Laser Ignition of Ultra-Lean Methane/Hydrogen/Air Mixtures at High Temperature and Pressure"; *Exptl. Therm. and Fluid Sci.*; 2005; 29:569-577.

Ma et al.; "Laser Spark Ignition and Combustion Characteristics of Methane-Air Mixtures"; *Combustion and Flame*; 1998; 112:492-506.

Klett et al.; "Ignition Characteristics of Methane-Air Mixtures Established Using a Rapid Compression Machine"; *ASRE Meeting*; Mar. 15-16, 2005; pp. 1-28.

Dale et al.; "Application of High Energy Ignition Systems to Engines"; *Prog. Energy Comb. Sci.*; 1997; 23:379-398.

Phuoc; "An Experimental and Numerical Study of Laser-Induced Spark in Air"; *Opt. and Lasers in Eng.*; 2005; 43:113-129.

Kandala et al.; "Computational Modeling of Localized Laser Energy Deposition in Quiescent Air"; *AIAA 2002-2160*; 2002; pp. 1-8.

Dors et al.; "Computational Fluid-Dynamic Model of Laser-Induced Breakdown in Air"; *Appl. Optics*; 2003; 42(30):5978-5985.

Rosen et al.; "Laser-Induced Breakdown in Nitrogen and The Rare Gases at 0.53 and 0.35 µm"; *J. Phys. D: Appl. Phys.*; 1987; 20:1264-1276.

Turcu et al.; "Measurement of KrF Laser Breakdown Threshold in Gases"; *Opt. Comm.*; 1997; 134:66-68.

Stakhiv et al.; "Laser Ignition of Engines via Optical Fibers?"; *Laser Physics*; 2004; 14(5):738-747.

Siegman; "Output Beam Propagation and Beam Quality From a Multimode Stable-Cavity Laser"; *IEEE J. Quant. Elect.*; 1993; 29(4):1212-1217.

Adelgren et al.; "Energy Deposition in Supersonic Flows"; *AIAA, Paper 2001-0885*; Jan. 2001.

Kono et al.; "Mechanism of Flame Kernel Formation Produced by Short Duration Sparks"; *Proceedings of the Combustion Institute*; 1989; pp. 1643-1649.

Morsy et al.; "Numerical Simulation of Front Lobe Formation in Laser-Induced Spark Ignition of $CH_4$/Air Mixtures"; *Proceedings of the Combustion Institute*; 2002; 29:1613-1619.

Bradley et al.; "The Measurement of Laminar Burning Velocities and Markstein Numbers for Iso-octane-Air and Iso-octane-n-Heptane-Air Mixtures at Elevated Temperatues and Pressures in an Explosion Bomb"; *Combustion and Flame*; 1998; 115:126-144.

Bradley et al.; "Spark Ignition and the Early Stages of Turbulent Flame Propagation"; *Combustion and Flame*; 1987; 69:71-93.

Kaminski et al. "Spark Ignition of Turbulent Methane/Air Mixtures Revealed by Time-Resolved Planar Laser-Induced Fluorescence and Direct Numerical Simulations"; *Proceedings of the Combustion Institute*; 2000; 28:399-405.

Dale et al.; "Laser Ignited Internal Combustion Engine—An Experimental Study"; *SAE 780329*; Feb./Mar. 1978.

Konorov et al.; "Laser Breakdown with Millijoule Trains of Picosecond Pulses Transmitted Through a Hollow-Core Photonic-Crystal Fibre"; *J. Physics D: Appl. Phys.*; 2003; 36:1375-1381.

Sato et al.; "Hollow-Waveguide-Based Transmission of Q-Switched Nd:YAG Laser Beam for Biological Tissue Ablation"; *SPIE Conference on Specialty Fiber Optics for Medical Applications*, San Jose, CA, *SPIE*; Jan. 1999; 3596:50-54.

Sato et aol. "Vacuum-Cored Hollow Waveguide for Transmission of High-Energy, Nanosecond Nd:YAG Laser Pulses and Its Application to Biological Tissue Ablation"; *Optics Letters*; 2000; 25(1):49-51.

Su et al.; "Beam Delivery By Large-Core Fibers: Effect of Launching Conditions on Near-Field Output Profile"; *Applied Optics*; Sep. 1992; 31(27):5816-5821.

Allison et al.; "Pulsed Laser Damage to Optical Fibers"; *Applied Optics*; 1985; 24(19):3140-3145.

Phuoc; "Laser Spark Ignition: Experimental Determination of Laser-Induced Breakdown Thresholds of Combustion Gases"; *Optics Communications*; 2000; 175:419-423.

Matsuura et al.; "Hollow Fibers for Delivery of Harmonic Pulses of Q-Switched Nd:YAG Lasers"; *Applied Optics*; Jan. 2002; 41(3):442-445.

Matsuura et al.; "Hollow-Fiber Delivery of High-Power Pulsed Nd:YAG Laser Light"; *Optics Letters*; Dec. 1998; 23(23):1858-1860.

Phuoc et al.;"Optical Characterization of the Laser-induced Spark In Air," *Optical Diagnostics in Engineering*; 2001; 5:12-26.

Ferioli, et al., "Laser-Induced Breakdown Spectroscopy for On-Line Engine Equivalence Ratio Measurements," *Applied Spectroscopy*; 2003; 57(9):1183-1189.

Morrell, et al.; "Interpretation of Optical Emissions for Sensors in Liquid Fueled Combustors"; *AIAA, Paper No. 2001-0787*; 2001; pp. 1-12.

Mitchell et al.; "Formaldehyde Formation in Large Bore Natural Gas Engines Part 1: Formation Mechanisms"; *Journal of Engineering for Gas Turbines and Power*; 2000; 122:603-610.

Olsen et al.; "Formaldehyde Formation in Large Bore Engines Part 2: Factors Affecting Measured $CH_2O$"; *Journal of Engineering for Gas Turbines and Power*; Oct. 2000; 122:611-616.

Frendi et al.; "Dependence of Minimum Ignition Energy on Ignition Parameters"; *Combustion Science and Technology*; 1990; 73:395-413.

Blanc et al.; "Ignition of Explosive Gas Mixtures by Electric Sparks. I. Minimum Ignition Energies and Quenching Distances of Mixtures of Methane, Oxygen and Inert Gases"; *The Journal of Chemical Physics*; 1947; 15(11):798-802.

DeMichelis; "Laser Induced Gas Breakdown: A Bibliographical Review"; *IEEE Journal of Quantum Electronics*; 1969; QE-5(4):188-202.

Fenn; "Lean Flammability Limit and Minimum Spark Ignition Energy"; *Industrial and Engineering Chemistry*; 1951; 43(12):2865-2869.

Ballal et al.; "The Influence of Flow Parameters on Minimum Ignition Energy and Quenching Distance"; *Proceedings of Fifteenth International Symposium on Combustion*; 1974; pp. 1473-1481.

Kim et al.; "Computational Modeling of Natural Gas Injection in a Large Bore Engine"; *J. Of Engineering for Gas Turbines and Power*; 2004; 126:656-664.

Kirkpatrick et al.; "Analytical and Computational Modeling of High-Pressure Gas Injection"; *Proceedings ASME ICE Fall Technical Conference, Paper No. 2001-ICE-410*; 2001; vol. 37-2, pp. 25-32.

Phuoc et al.; 2002; "Laser-induced Spark for Measurements of the Fuel-to-Air Ratio of a Combustible Mixture," *Fuel*; 81, pp. 1761-1765.

Harilal et al.; "Diagnostics of Laser Induced Spark in Air Using Fast ICCD Photography"; *Internal Lab Report, Paper No. UCSD-LPLM-02-01, Fusion Division Center for Energy Research*, University of California, San Diego, CA; 2002.

Schnieder; "Techniques and Applications of Laser Spark Spectroscopy"; *Laser 83 Conference Proceedings*; 1982.

Ottesen et al.; "Real-Time Laser Spark Spectroscopy of Particulates in Combustion Environments"; *Applied Spectroscipy*; 1989; 43(6):967-976.

Chan et al.; "Spectrum Estimation and Noise Reduction for Laser Induced Breakdown Spectroscopy"; *MS State DSP Conference, Spectral Analysis Group: LIBS*; Fall 1995; pp. 21-33.

Furlong et al. "Combustion Control Using a Multiplexed Diode-Laser Sensor System"; *American Institute of Aeronautics and Astronautics*; 1996; p. 1-6.

Armstrong et al. "Spectroscopic Investigation of Laser-Initiated Low-Pressure Plasma in Atmospheric Gases"; *Applied Optics*; 1983; 22(10):1573-1577.

Phuoc et al.; "Laser Spark Ignition of a Jet Diffusion Flame"; *Combustion and Flame*, date unknown.

Forsich et al.; "Characterization of Laser-Induced Ignition of Biogas-Air Mixtures"; *Biomass and Energy*; 2004; 27:299-312.

Dors et al.; "Fluid Dynamics Effects Following Laser-Induced Optical Breakdown"; *AIAA 2000-0717*; 2000.

Lackner et al.; "In Situ Investigation of Laser-Induced Ignition and the Early Stages of Methane-Air Combustion at High Pressures Using a Rapidly Tuned Diode Laser at 2.55 μm"; *Spectrochimica Acta Part A*; 2003; 59:2997-3018.

Kopecek et al.; "Laser-Induced Ignition of Methane-Air Mixtures at Pressures Up To 4 MPa"; *Laser Physics*; 2003; 13(11):1365-1369.

Kravchik et al.; "Numerical Modeling of Spark Ignition and Flame Initiation in a Quiescent Methane-Air Mixture"; *Combustion and Flame*; 1994; 99:635-643.

Borghese et al.; "Time-Resolved Spectral and Spatial Description of Laser-Induced Breakdown in Air as a Pulsed, Bright, and Broadband Ultraviolet-Visible Light Source"; *Applied Optics*; 1998; 37(18):3977-3981.

Maas et al.; "Observation and Simulation of Laser-Induced Ignition Processes in $O_2$-$O_3$ and $H_2$-$O_2$ Mixtures"; *Twenty-First Symposium (International) on Combustion/The Combustion Institute*; 1986; pp. 1869-1876.

Forch et al.; "Laser-Based Ignition of $H_2/O_2$ and $D_2/O_2$ Premixed Gases Through Resonant Multiphoton Excitation of H and D Atoms Near 243 nm"; *Combustion and Flame*; 1991; 85:254-262.

Van Stryland et al.; "Pulse-Width and Focal-Volume Dependence of Laser-Induced Breakdown"; *Physical Review B*; 1981; 23(5):2144-2151.

Willems et al.; "Modeling the Initial Growth of the Plasma and Flame Kernel in SI Engines"; *ICE* vol. 2001, 36-2 *ASME 2001*; p. 1-7.

Forch et al.; "Ultraviolet Laser Ignition of Premixed Gases by Efficient and Resonant Multiphoton Photochemical Formation of Microplasmas"; *Combustion Science and Technology*; 1987; 52:151-159.

Trott; "$CO_2$—Laser-Induced Deflagration of Fuel/Oxygen Mixtures[a]"; *J. Appl. Phys.*; 1983; 54(1):118-130.

Sloane; "Energy Requirements for Spherical Ignitions in Methane-Air Mixtures at Different Equivalence Ratios"; *Combustion Science and Technology*; 1990; 73:351-365.

Weinberg et al.; "A Preliminary Investigation of the Use of Focused Laser Beams for Minimum Ignition Energy Studies"; *Proc. Roy. Soc. Lond. A.*; 1971; 321:41-52.

Santavicca et al.; "Laser Induced Spark Ignition of Methane-Oxygen Mixtures"; *First Technical Report for NASA Grant NAG3-966*; 1991.

Schmieder; Laser Spark Ignition and Extinction of a Methane-Air Diffusion Flame; *J. Appl. Phys.*; 1981; 52(4):3000-3003.

Lavid et al.; "Photochemical Ignition of Premixed Hydrogen/Oxygen Mixtures with ArF Laser"; *Combustion Science and Technology*; 1994; 96:231-245.

Hardalupas et al.; "Chemiluminescence Sensor for Local Equivalence Ratio of Reacting Mixtures of Liquid Fuel Vapor and Air (Mast B Liquid)" www.Cheng.cam.ac.uk/research/groups/1a; pp. 1-12, 2004.

Morsy et al.; "Laser-Induced Ignition Using a Conical Cavity in $CH_4$/Air Mixtures"; *Combustion and Flame*; 1999; 119:473-482.

Morsy et al.; "Laser-Induced Two-Point Ignition of Premixture With a Single-Shot Laser"; *Combustion and Flame*; 2001; 125:724-727.

Gupta et al.; "Laser Based Ignition for Reciprocating Natural Gas Engines: Preliminary Experimental Study"; *Argonne National Laboratory, LBIS Round Table Meeting*; 2002.

Kohse-Höinghaus et al.; "Combustion at the Focus: Laser Diagnostics and Control"; *Proceedings of the Combustion Institute*; 2005; 30:89-123.

Thiele et al.; "Numerical Simulation of Spark Ignition Including Ionization"; *Proceedings of the Combustion Institute*; 2000; 28:1177-1185.

Yasar; "A New Ignition Model for Spark-Ignition Engine Simulations"; *Parallel Computing*; 2001; 27:179-200.

Herdin et al.; "Laser Ignition a New Concept to Use and Increase the Potentials of the Gas Engines"; *General Electric, 2nd Annual Advanced Stationary Reciprocating Engines Conference*; 2005, pp. 1-35.

Starik et al.; "Possibility of Initiation of Combustion of $CH_4$-$O_2$ (Air) Mixtures with Laser-Induced Excitation of $O_2$ Molecules"; *Combustion, Explosion, and Shock Waves*; 2004; 40(5):499-510.

Zizak; "Flame Emission Spectroscopy: Fundamentals and Applications"; *ICS Training Course on Laser Diagnostics and Combustion Processes*; Nov. 2000.

Yuasa; "Effects of Energy Deposition Schedule on Minimum Ignition Energy in Spark Ignition of Methane/Air Mixtures"; *Proceedings of the Combustion Institute*; 2002; 29:743-750.

Beretta et al.; "Turbulent Flame Propagation and Combustion in Spark Ignition Engines"; *Combustion and Flame*; 1983; 52:217-245.

Simmie; "Detailed Chemical Kinetic Models for the Combustion of Hydrocarbon Fuels"; *Progress in Energy and Combustion Science*; 2003; 29:599-634.

Gatowski et al.; "Flame Photographs in a Spark-Ignition Engine"; *Combustion and Flame*; 1984; 56:71-81.

Richou et al.; "Delivery of 10-MW Nd:YAG Laser Pulses by Large-Core Optical Fibers: Dependence of the Laser-Intensity Profile on Beam Propagation"; *Applied Optics*; Mar. 1997; 36(7):1610-1614.

Alda et al.; "Characterization of Aberrated Laser Beams"; *J. Opt. Soc. Am. A.*; 1997; 14(10):2737-2747.

Green; "Beam Focusability Factor- A New Monitoring Tool for Increased Profitability"; *Lasers in Manufacturing*; 2002; vol. 28.

Koplow et al.; "Single-Mode Operation of a Coiled Multimode Fiber Amplifier"; *Optics Letters*; 2000; 25(7):442-444.

Potyrailo et al.; "Near-Ultraviolet Evanescent-Wave Absorption Sensor Based on a Multimode Optical Fiber"; *Analytical Chemistry*; 1998; 70:1639-1645.

Galvanauskas; "High Power Fiber Lasers"; *Optics and Photonics News*; 2004; pp. 42-47.

Hand et al.; "Fibre Optic Beam Delivery System for High Peak Power Laser PIV Illumination"; *Meas. Sci. Technol.*; 1999; 10:239-245.

Trott et al.; "High-Power Nd: Glass Laser Transmission Through Optical Fibers and Its Use in Acceleration of Thin Foil Targets"; *J. Applied Physics*; 1990; 67(7):3297-3301.

Hongo et al.; "Transmission of Kilowatt-Class $CO_2$ Laser Light Through Dielectric-Coated Metallic Hollow Waveguides for Material Processing"; *Applied Optics*; 1992; 31(24):5114-5120.

Hunter et al.; "Selecting a High-Power Fiber-Optic Laser Beam Delivery System"; *Laser Institute of America, Proceedings ICALEO*; 1996; 81E:173-182.

Schmidt-Uhlig et al.; "New Simplified Coupling Scheme for the Delivery of 20 MW Nd: YAG Laser Pulses by Large Core Optical Fibers"; *Applied Physics B*; 2001; 72:183-186.

Moulton; "New Technologies of Solid State Lasers for Materials Processing"; *Q-Peak Applied Photonic Systems*; 2004.

Moar et al.; "Fabrication, Modeling, and Direct Evanescent Field Measurement of Tapered Optical Fiber Sensors"; *Journal of Applied Physics*; 1999; 85(7):3395-3398.

Matsuura et al.; "Optical Properties of Small-Bore Hollow Glass Waveguides"; *Applied Optics*; 1995; 34(30):6842-6847.

Dai et al.; "High-Peak-Power, Pulsed $CO_2$ Laser Light Delivery by Hollow Glass Waveguides"; *Applied Optics*; 1997; 36(21):5072-5077.

Mohebbi et al.; "Silver-Coated Hollow-Glass Waveguide for Applications at 800 nm"; *Applied Optics*; 2002; 41(33):7031-7035.

Bihari et al.; "Development of Advanced Laser Ignition System for Stationary Natural Gas Reciprocating Engines"; *ASME, Paper ICEF2005-1325*; 2005; pp. 1-8.

Siegman; "Analysis of Laser Beam Quality Degradation Caused by Quartic Phase Aberrations"; *Applied Optics*; 1993; 32(30):5893-5901.

Sturm et al.; "Optical Fiber Transmission of Multiple Q-Switch Nd: YAG Laser Pulses with Microsecond Interpulse Separations"; *Applied Physics B*; 1996; 63:363-370.

Abdel-Gayed ed al.; Criteria for Turbulent Propagation Limits of Premixed Flames; *Combustion and Flame*; 1985; 62:61-68.

Ahrens et al; Development of an Open Path Laser Ignition System for a Large Bore Natural Gas Engine: Part 2 Single Cylinder Demonstration; *ASME*; 2005 Fall Technical Conference ICEF2005 Proceedings; ICES2005-1317:1-9.

Alda et al; Characterization of Aberrated Laser Beams; *Optical Society of America*; 1997; 14(10):2737-2747.

Ballal et al; The Influence of Flow Parameters on Minimum Ignition Energy and Quenching Distance; *Proceedings of Fifteenth International Symposium on Combustion*; 1974; 1473-1481.

Beduneau et al; Measurements of Minimum Ignition Energy in Premixed Lamina Methane/Air Flow by Using Laser Induced Spark; *Combustion and Flame*; 2003; 132:653-665.

Beretta et al; Turbulent Flame Propagation and Combustion in Spark Ignition Engines; *Combustion and Flame*; 1983; 52:217-245.

Bihari et al; Development of Advanced Laser Ignition System for Stationary Natural Gas Reciprocating Engines; *ASME*; 2005 Fall Technical Conference ICEF2005 Proceedings; ICEF2005-1325:1-8.

Biruduganti et al; Performance Analysis of a Natural Gas Generator Using Laser Ignition; *ASME*; 2004 Fall Technical Conference ICEF04; ICEF2004-983:1-7.

Borghi, R.; On the Structure and Morphology of Turbulent Premixed Flames; *Recent Advances in Aerospace Sciences; in Honor of Luigi Crocco on His Seventy-Fifth Birthday*; 1985; Chapter 7:117-138.

Bradley et al; Fundamentals of High-Energy Spark Ignition with Lasers; *Combustion and Flame*; 2004; 138:55-77.

Bradley et al; Spark Ignition and the Early States of Turbulent Flame Propagation; *Combustion and Flame*; 1987; 69:71-93.

Bradley et al; The Measurement of Laminar Burning Velocities and Markstein Numbers for Iso-octane-Air and Iso-octane-n-Heptane-Air Mixtures at Elevated Temperatures and Pressures in an Explosion Bomb; *Combustion and Flame*; 1998; 115:126-144.

Buchter, S.; Advances Lead to Miniature Supercontinuum Sources; *Photonics Spectra*; 2004;38(10):46,49.

Chen et al; Spatial and Temporal Profiles of Pulsed Laser-Induced Air Plasma Emissions; *Journal of Quantitative Spectroscopy & Radiative Transfer*; 2000; 67:91-103.

Chen et al; Visualization of Laser-Induced Breakdown and Ignition; *Optics Express*; 2001; 9(7):360-372.

Dai et al; High-Peak-Power, Pulsed $CO_2$ Laser Light Delivery by Hollow Glass Waveguides; *Applied Optics*; 1997; 36(21):5072-5077.

Davis et al; Laser-Induced Plasma Formation in Xe, Ar, $N_2$, and $O_2$ at the First Four Nd:YAG Harmonics; *Applied Optics*; 1991; 30(30):4358-4364.

Dors et al; Computational Fluid-Dynamic Model of Laser-Induced Breakdown in Air; *Applied Optics*; 2003; 42(30):5978-5985.

Forsich et al; Characterization of Laser-Induced Ignition of Biogas-Air Mixtures; *Biomass & Bioenergy*; 2004; 27:299-312.

Galt et al; Optical Breakdown in Fused Silica and Argon Gas: Application to Nd:YAG Laswer Limiter; *Applied Optics*; 2003; 42(3):579-584.

Galvanauskas, A.; High Power Fiber Lasers; *Optics & Photonics News*; 2004; July:42-47.

Gamal et al; A Numerical Investigation of the Dependence of the Threshold Irradiance on the Wavelength in Laser-Induced Breakdown in $N_2$; *J. Phys. D: Appl. Phys*; 1999; 32:423-429.

Gatowski et al; Flame Photographs in a Spark-Ignition Engine; *Combustion and Flame*; 1984; 56:71-81.

Glumac et al; Temporal and Spatial Evolution of a Laser Spark in Air; *AIAA Journal*; 2005; 43(9):1984-1993.

Green, L.; Beam Focusability Factor—A New Monitoring Tool for Increased Profitability; *Lasers in Manufacturing, The Industrial Laser User*; 2002; 28:2 pages.

Hand et al; Fibre Optic Beam Delivery System for High Peak Power Laser PIV Illumination; *Meas. Sci. Technol.*; 1999; 10:239-245.

Herdin et al; Laser Ignition—A New Concept to Use and Increase the Potentials of Gas Engines; *ASME*; 2005 Fall Technical Conference Proceedings of ICEF2005; ICEF2005-1352:1-9.

Herdin, G.; Laser Ignition a New Concept to Use and Increase the Potentials of the Gas Engines; *GE Jenbacher*; 2005; 35 pages.

Hongo et al; Transmission of Kilowatt-Class $CO_2$ Laser Light Through Dielectric-Coated Metallic Hollow Waveguides for Material Processing; *Applied Optics*; 1992; 31(24):5114-5120.

Hunter, et al; Selecting a High-Power Fiber-Optic Laser Beam Delivery System; *Laser Institute of America*; 1996; 81E:173-182.

Gaborel et al; Toward the Development of a Laser Ignition System for Aircraft Engines; *1st Workshop INCA*, Villaroche, France; 2005; 1-8.

Kaminski et al; Spark Ignition of Turbulent Methane/Air Mixtures Revealed by Time-Resolved Planar Laser-Induced Fluorescence and Direct Numerical Simulations; *Proceedings of the Combustion Institute*; 2000; 28:399-405.

Klett et al; Ignition Characteristics of Methane-air Mixtures Established Using a Rapid Compression Machine; *Argonne National Laboratory*; 2005 ASRE Meeting; 28 pages.

Kliner et al; Fiber Laser Technology Reels in High Power Results; *SPIE's oemagazine*; 2004; January:32-35.

Kohse-Hoinghaus et al; Combustion at the Focus: Laser Diagnostics and Control; *Proceedings of the Combustion Institute*; 2004; 30:89-123.

Kono et al; Mechanism of Flame Kernel Formation Produced by Short Duration Sparks; *Twenty-Second Symposium (International) on Combustion/The Combustion Institute*; 1988; 1643-1649.

Konorov et al; Laser Breakdown with Millijoule Trains of Picosecond Pulses Transmitted Through a Hollow-Core Photonic-Crystal Fibre; *Journal of Physics D*; 2003; 36:1375-1381.

Kopecek et al; Laser Ignition of Methane-Air Mixtures at High Pressures; *Experimental Thermal and Fluid Science*; 2003; 27:499-503.

Kopecek et al; Laser Ignition of Methane-Air Mixtures at High Pressures and Diagnostics; *Journal of Engineering for Gas Turbines and Power*; 2005; 127:213-219.

Koplow et al; Single-mode Operation of a Coiled Multimode Fiber Amplifier; *Optics Letters*; 2000; 25(7):442-444.

Kravchik et al; From Spark Ignition to Flame Initiation; *Combust. Sci. And Tech.*; 1995; 108:1-30.

Lackner et al; Investigation of the Early Stages in Laser-Induced Ignition by Schlieren Photography and Laser-Induced Fluorescence Spectroscopy; *Optics Express*; 2004; 12(19):4546-4557.

Lackner et al; Laser Ignition in Internal Combustion Engines—A Contribution to a Sustainable Environment; *Institute of Chemical Engineering*; no date; 18 pages.

Lee et al; Laser Spark Ignition of Chemically Reactive Gases; *AIAA Journal*; 7(2):312-317, 1969.

Liedl et al; Laser Induced Ignition of Gasoline Direct Injection Engines; *Institute for Forming- and High Power Laser Technology*; Arsenal Obj. 207(1030):6 pages, 2005.

Limpert et al; 100-W Average-Power, High-Energy Nanosecond Fiber Amplifier; *Applied Physics B*; 2002; 75:477-479.

Longenecker et al; Laser-Generated Spark Morphology and Temperature Records from Emission and Rayleigh Scattering Studies; *Applied Optics*; 2003; 42(6):990-996.

McMillian et al; Laser Spark Ignition: Laser Development and Engine Testing; *ASME*; 2004 Fall Technical Conference ICEF04 Proceedings; ICEF2004-917:1-10.

Maly, R.; Spark Ignition: Its Physics and Effect on the Internal Combustion Engine; *Fuel Economy in Road Vehicles Powered by Spark Ignition Engines*; 1984; Chapters 3-4:91-149; Figs 1-16B.

Maly et al; Initiation and Propagation of Flame Fronts in Lean $CH_4$-Air Mixtures by the Three Modes of the Ignition Spark; *Inhibition and Ignition (Proceedings of Seventeenth International Symposium on Combustion)*; 1976; 821-831.

Matsuura et al; Hollow-Fiber Delivery of High-Power Pulsed Nd:YAG Laser Light; *Optics Letters*; 1998; 23(23):1858-1860.

Matsuura et al; Hollow Fibers for Delivery of Harmonic Pulses of Q-Switched Nd:YAG Lasers; *Applied Optics*; 2002; 41(3):442-445.

Matsuura et al; Low Order Multimode Generation in Hollow Glass Waveguides; *Electronics Letters*; 1996; 32(12):1096-1098.

Matsuura et al; Optical Properties of Small-Bore Hollow Glass Waveguides; *Applied Optics*; 1995; 34(30):6842-6847.

Moar et al; Fabrication, Modeling, and Direct Evanescent Field Measurement of Tapered Optical Fiber Sensors; *Journal of Applied Physics*; 1999; 85(7):3395-3398.

Mohebbi et al; Silver-Coated Hollow-Glass Waveguide for Applications at 800 nm; *Applied Optics*; 2002; 41(33):7031-7035.

Morgan, C.G.; Laser-Induced Breakdown of Gases; *Rep. Prog. Phys.*; 1975; 38:621-665.

Morsy et al; Numerical Simulation of Front Lobe Formation in Laser-Induced Spark Ignition of $CH_4$/Air Mixtures; *Proceedings of the Combustion Institute*; 2002; 29:1613-1619.

Moulton, P.; New Technologies of Solid State Lasers for Materials Processing; *Q-Peak Applied Photonic Systems*; 2004 (PhAST); 50 pages.

Niemz, M.H.; Threshold Dependence of Laser-Induced Optical Breakdown on Pulse Duration; *Appl. Phys. Lett.*; 1995; 66(10):1181-1183.

Nubling et al; Launch Conditions and Mode Coupling in Hollow-Glass Waveguides; *Optical Engineering*; 1998; 37(9):2454-2458.

Oriel Instruments; Light Collection and System Throughput; *Oriel Instruments Catalog/Light Sources*; no date; 1-19 through 1-15.

Phuoc, T.; A Comparative Study of the Photon Pressure Force, the Photophoretic Force, and the Adhesion Van Der Waals Force; *Optics Communications*; 2005; 245:27-35.

Phuoc, T.; An Experimental and Numerical Study of Laser-Induced Spark in Air; *Optics and Lasers in Engineering*; 2005; 43:113-129.

Phuoc et al; Laser-Induced Spark for Measurements of the Fuel-to-air Ratio of a Combustible Mixture; *Fuel*; 2002; 81:1761-1765.

Phuoc, T.; Laser-Induced Spark Ignition Fundamental and Applications; *Optics and Lasers in Engineering*; 2006; 44:351-397.

Phuoc et al; Laser-Induced Spark Ignition of $CH_4$/Air Mixtures; *Combustion and Flame*; 1999; 119:203-216.

Phuoc, T.; Laser Spark Ignition: Experimental Determination of Laser-Induced Breakdown Thresholds of Combustion Gases; *Optics Communications*; 2000; 175:419-423.

Phuoc, T.; Single-Point Versus Multi-Point Laser Ignition: Experimental Measurements of Combustion Times and Pressures; *Combustion and Flame*; 2000; 122:508-510.

Potyrailo et al; Near Ultraviolet Evanescent-Wave Absorption Sensor Based on a Multimode Optical Fiber; *Analytical Chemistry*; 1998; 70(8):1639-1645.

Quader, A.; What Limits Lean Operation in Spark Ignition Engines—Flame Initiation or Propagation?; *SAE Transactions*; 1976; SAE Paper 760760:2374-2387.

Richardson et al; Laser Spark Ignition of a Blended Hydrogen-Natural Gas Fueled Single Cylinder Engine; *ASME*; 2006 Spring Technical Conference ICES2006 Proceedings; ICES2006-1397:1-9.

Richou et al; Delivery of 10-MW Nd:YAG Laser Pulses by Large-Core Optical Fibers: Dependence of the Laser-Intensity Profile on Beam Propagation; *Applied Optics*; 1997; 36(7):1610-1614.

Ronney, P.; Laser Versus Conventional Ignition of Flames; *Optical Engineering*; 33(2):510-521, 1994.

Rosen et al; Laser-Induced Breakdown in Nitrogen and the Rare Gases at 0.53 and 0.35 µm; *J. Phys. D.:Appl. Phys.*; 1987; 20:1264-1276.

Roundy, C.; Propagation Factor Quantifies Laser Beam Performance; *Laser Focus World/Beam Profile Analysis*; 1999; 3 pages.

Ruff et al; Measurement of Beam Quality Degradation Due to Spherical Aberration in a Simple Lens; *Optical and Quantum Electronics*; 1994; 26:629-632.

Sato et al; Hollow-Waveguide-Based Transmission of Q-Switched Nd:YAG Laser Beam for Biological Tissue Ablation; *SPIE Conference on Specialty Fiber Optics for Medical Applications*; 1999; SPIE 3596:50-54.

Sato et al; Vacuum-Cored Hollow Waveguide for Transmission of High-Energy, Nanosecond Nd:YAG Laser Pulses and its Application to Biological Tissue Ablation; *Optics Letters*; 2000; 25(1):49-51.

Schmidt-Uhlig et al; New Simplified Coupling Scheme for the Delivery of 20 MW Nd:YAG Laser Pulses by Large Core Optical Fibers; *Applied Physics B*; 2001; 72:183-186.

Shephard et al; Improved Hollow-Core Photonic Crystal Fiber Design for Delivery of nanosecond Pulses in Laser Micromachining Applications; *Applied Optics*; 2005; 44(21):4582-4587.

Siegman, A.E.; Analysis of Laser Beam Quality Degradation Caused by Quartic Phase Aberrations; *Applied Optics*; 1993; 32(30):5893-5901.

Siegman, A.E.; How to "Maybe" Measure Laser Beam Quality; *Optical Society of America Annual Meeting Tutorial Presentation*; 1997: October:18 pages.

Siegman, A.E.; How to (Maybe) Measure Laser Beam Quality; *CREOL*; 2004; April:50 pages.

Siegman et al; Output Beam Propagation and Beam Quality from a Multimode Stable-Cavity Laser; *IEEE Journal of Quantum Electronics*; 1993; 29(4):1212-1217.

Simmie, J.; Detailed Chemical Kinetic Models for the Combustion of Hydrocarbon Fuels; *Progress in Energy and Combustion Science*; 2003; 29:599-634.

Sircar et al; Laser Induced Breakdown of Ar, $N_2$ and $O_2$ gases using 1.064, 0.532, 0.355 and 0.266 µm Radiation; *Applied Physics B*; 1996; 63:623-627.

Sjoberg et al; Dependence of Stimulated Brillouin Scattering in Multimode Fibers on Beam Quality, Pulse Duration, and Coherence Length; *Optical Society of America*; 2003; 20(3):434-442.

Sloane, T.; Energy Requirements for Spherical Ignitions in Methane-Air Mixtures at Different Equivalence Ratios; *Combust. Sci. And Tech.*; 1990; 73:351-365.

Spiglanin et al; Time-Resolved Imaging of Flame Kernels: Laser Spark Ignition of $H_2/O_2$/Ar Mixtures; *Combustion and Flame*; 1995; 102:310-328.

Stachowicz et al; Design and Development of Waukesha's, Stoichiometric, Cooled EGR Engine for the California ARICE Program; *ASME*; 2005 Fall Technical Conference of ICEF2005 Proceedings; ICEF2005-1329:1-11.

Stakhiv et al; Laser Ignition of Engines Via Optical Fibers?; *Laser Physics*; 2004; 14(5):738-747.

Starik et al; Possibility of Initiation of Combustion of $CH_4$-$O_2$ (air) Mixtures with Laser-Induced Excitation of $O_2$ Molecules; *Combustion, Explosion, and Shock Waves*; 2004; 40(5):499-510.

Sturm et al; Optical Fiber Transmission of Multiple Q-Switch Nd:YAG Laser Pulses with Microsecond Interpulse Separations; *Applied Physics B*; 1996; 63:363-370.

Su et al; Beam Delivery by Large-Core Fibers: Effect of Launching Conditions on Near-Field Output Profile; *Applied Optics*; 1992; 31(27):5816-5821.

Tambay et al; Laser-Induced Breakdown Studies of Laboratory Air at 0.266, 0.355, 0.532, and 1.06 μm; *J. Appl. Phys.*; 1991; 70(5):2890-2892.

Thiele et al; Numerical Simulation of Spark Ignition Including Ionization; *Proceedings of the Combustion Institute*; 2000; 28:1177-1185.

Tran et al; Optical Characterization of the Laser-Induced Spark in Air; *National Energy Technology Laboratory U.S. Department of Energy*; no date; 1-14.

Trinh et al; Dual-Laser-Pulse Ignition; *Photonics Tech Briefs*; 2006; January:14a, 15a.

Trott et al; High-Power Nd:Glass Laser Transmission Through Optical Fibers and its Use in Acceleration of Thin Foil Targets; *J. Appl. Phys.*; 1990; 67(7):3297-3301.

Turcu et al; Measurement of KrF Laser Breakdown Threshold in Gases; *Optics Communications*; 1997; 134:66-68.

Tzortzakis et al; Femtosecond Laser-Guided Electric discharge in Air; *Laboratoire d'Optique Appliquee*; no date; CNRS UMR 7639: 2 pages.

Van Stryland et al; Pulse-Width and Focal-Volume Dependence of Laser-Induced Breakdown; *Physical Review B*; 1981; 23(5):2144-2151.

Weinrotter et al; Laser Ignition of Ultra-Lean Methane/Hydrogen/Air Mixtures at High Temperature and Pressure; *Experimental Thermal and Fluid Science*; 2005; 29:569-577.

Williams et al; Picosecond Air Breakdown Studies at 0.53 μm; *Appl. Phys. Lett.*; 1983; 43(4):352-354.

Yalin et al; Development of a Fiber Delivered Laser Ignition System for Natural Gas Engines; *ASME*; 2006 Spring Technical Conference ICES2006 Proceedings; ICES2006-1370:1-6.

Yalin et al; Laser Ignition of Natural Gas Engines Using Fiber Delivery; *ASME*; 2005 Fall Technical Conference ICEF2005 Proceedings; ICEF2005-1336:1-9.

Yasar, O.; A New Ignition Model for Spark-Ignited Engine Simulations; *Parallel Computing*; 2001; 27:179-200.

Yuasa et al; Effects of Energy Deposition Schedule on Minimum Ignition Energy in Spark Ignition of Methane/Air Mixtures; *Proceedings of the Combustion Institute*; 2002; 29:743-750.

Zizak, G.; Flame Emission Spectroscopy: Fundamentals and Applications; *ICS Training Course on Laser Diagnostics of Combustion Processes, NILES*, University of Cairo, Egypt; 2000; November:29 pages.

\* cited by examiner

FIBER COUPLED OPTICAL SPARK DELIVERY SYSTEM

CROSS REFERENCE TO RELATED APPLICATION

The present application claims the benefit of U.S. Provisional Application No. 60/598,932 filed on Aug. 4, 2004, the entire disclosure of which is incorporated herein by reference in its entirety.

STATEMENT REGARDING FEDERALLY SPONSORED RESEARCH OR DEVELOPMENT

This invention was made with United States Government support under Grant No. DE-FC26-02NT41335 awarded by the Department of Energy. The United States Government may have certain rights in the invention.

FIELD OF THE INVENTION

The present invention relates to a device and method for creating a spark, and more particularly, to device and method for creating a spark using a laser and hollow optical fiber.

BACKGROUND OF THE INVENTION

Pulsed lasers producing optical pulses with short temporal duration and high peak powers may be used to create laser sparks and initiate combustion. When the pulsed laser beam is focused to a small point, the intensity (power per area) at that point can be large enough to initiate electrical breakdown in the gas, thereby forming a spark (plasma). The physical mechanisms postulated for breakdown include photochemical absorption, multi-photon ionization, and electron cascade.

In an electron cascade, it is assumed that a small number of electrons appear in the beam focus region. These electrons acquire energy from the electric field by absorption of photons, and collide with neutral atoms, a process termed "inverse bremsstrahlung". The electrons ionize the gas when their energy exceeds the ionization potential of the atoms. The electron collision will ionize the atom, producing additional electron(s) to start the cascade process and lead to avalanche breakdown.

The minimum amount of energy or intensity required to cause the breakdown is commonly referred to as the breakdown threshold. For nano second pulse durations and milli joule energy levels, breakdown is thought to be intensity limited. In addition, the breakdown threshold is also dependent on the gas composition and pressure existing in the spark target environment.

Experimental measurements of spatially and temporally averaged optical intensities are found by dividing the laser power (pulse energy/pulse duration) by the beam area. At the spark location the beam area is typically small, with dimensions on the order of 10 to 100 µm, and in many experiments it has not been precisely measured. Therefore, there tends to be some uncertainty in published intensity requirements for breakdown and spark formation. Additional uncertainty in intensity requirements is due to spatial and temporal averaging. For conditions of interest, including nano second pulse durations and milli joule energy levels with a target sparking environment comprising low-particulate (or particulate free) gas mixtures with a significant fraction of air and pressures of approximately 1 to 30 atmospheres, the required optical intensity to spark is approximately 0.5 to $10 \times 10^{11}$ W/cm$^2$.

For sparking uses associated with combustion engines, the desired combination of lean mixtures and high brake mean effective pressure results in the cylinder pressure and mixture density in modern engines being relatively high, creating difficulties for traditional spark ignition systems. As the density increases in the cylinder, the breakdown voltage (minimum voltage required to form a spark using a spark ignition system) also increases, ultimately to such high voltage levels that traditional spark ignition systems encounter problems with dielectric breakdown leading to unwanted sparking from the ignition leads and other undesired locations (i.e., the spark does not form between the electrodes as intended). Even if the high voltage can be managed, high voltage means that electrode erosion can be quite high. The combination of spark plug erosion and dielectric breakdown is a limiting factor in the operational envelope of modern gas engines. Optical sparks suffer from neither of these shortcomings and thus may have significant advantages for improved engine operation. In certain cases, optical sparks can also afford performance benefits associated with extension of maintenance intervals as well as changes in the lean limit, coefficient of variation of pressure, pollutant emissions, and other parameters.

Laser ignition has been shown to be a particularly effective way of igniting lean mixtures. It is fairly easy to create a spark by using "open path" laser delivery. The open path method implies that the laser beam propagates through the ambient air and is steered to the desired location by mirrors. Although simple and effective, this system is not practical for most industrial applications. Thus, there is a need for development and demonstration of a fiber optic delivery system.

The key challenges associated with the use of fiber optic delivery are the intensity damage threshold of the fiber optic material and limitations on focusing fiber optically delivered light. The former point relates to material properties of fiber material, typically silica, and limits the maximum achievable optical intensity at the fiber exit to approximately 1 to $5 \times 10^9$ W/cm$^2$. Generally, the desired spark location is not right at the fiber exit, but is located some distance downstream of the fiber exit, so that intermediate optics are used to capture the light leaving the fiber and to focus it at the desired spark location. Because the intensity at the fiber exit is limited, the imaging or focusing requirements to generate a sufficient intensity to spark at the desired spark location become more stringent. In other words, the light exiting the fiber must be demagnified to enable a sufficiently high optical intensity that exceeds the breakdown threshold at the desired spark location.

The problem is compounded by the second challenge which is the difficulty in focusing fiber optically delivered light. The minimum achievable spot size (i.e. beam dimension at the focal spot) tends to increase for a laser beam that has passed through a fiber optic. This increase in minimum achievable spot size, which makes it more difficult to reach high intensity, is related to a degradation of the spatial quality of a laser beam caused by transmission through a fiber. The spatial quality of a laser beam, typically characterized by its $M^2$ parameter, is a function of the transverse spatial modes of which the beam is composed. (A low $M^2$ parameter corresponds to a beam composed of "lower order" spatial modes, and such modes can be focused to smaller dimensions.) Generally, the $M^2$ parameter of the beam exiting the fiber is relatively large, and larger than the value for the beam entering the fiber. The spatial quality (and $M^2$) of light exiting a fiber is influenced by the fiber diameter and the exit angle of light leaving the fiber. For small-diameter single-mode fibers (diameter<~30 µm) the degradation is minimal; however, such fibers cannot transmit a large amount of energy and are not considered useful in laser ignition application(s). Larger diameter fibers are required to transmit higher energies, but in such cases the larger diameter increases the beam degradation and thus impedes focusing to small spot sizes (high intensities).

Solid core fiber optics have one optical material in the core (center channel) and a second optical material in the cladding (surrounding material). The index-of-refraction of the core material is selected to be larger than that of the cladding material so that light at the core-cladding interface is "totally internally reflected" and thus guided through the fiber core. Hollow core fibers have a hollow bore (no material) surrounded by a wall material. Such a configuration has a higher index in the wall than the core and does not allow efficient light guiding. Uncoated hollow fibers may only be effectively used in straight geometries.

Finally, it noted that it is much more difficult to form a spark in the gas phase as compared to on a solid or in a liquid because more optical intensity is required. There are a number of papers/approaches that form sparks off solid surfaces after fiber delivery, and this can be done rather "routinely" with a solid fiber. For the same reason, it is also routine to spark in gases containing dust, sprays, or particulate matter since the spark initially forms on those liquids/solids as opposed to in the gas. However, it is desirable to spark in the gas phase because it allows the spark to be located away from cylinder walls or other solid surfaces, which act as heat sinks and yield poorer combustion performance. Freedom in locating the spark may also allow sparking at other locations that offer other combustion benefits (for example, locations where the air/fuel mixing is better or the gas velocity field is favorable).

Another consequence of the ease of sparking on solids is that the use of fiber optics becomes harder because of the tendency to spark (unwantedly) at the launch entrance of the fiber. Such sparks consume energy from the laser beam and may degrade the quality of the beam preventing subsequent sparking after the fiber

SUMMARY OF THE INVENTION

The present invention is generally directed to solving these and other problems of the prior art. In accordance with embodiments of the present invention, a system for generating a spark is provided, including generating a spark in a combustion chamber of an internal combustion engine. Embodiments of the present invention provide for a laser beam that is launched into, and passed through, a hollow fiber. The beam exits the fiber and is demagnified (focused) using exit or downstream optics, thereby producing a spark. Embodiments of the present invention allow the spark to be moved away from the relatively cold spark plug electrodes and combustion chamber walls, thus removing two of the "heat sinks" that can slow down early flame growth in a conventional spark ignition engine and allowing the spark to be positioned at other locations which may provide other combustion benefits. The spark formation process is not initiated by high voltage, so the problems of dielectric breakdown and spark plug erosion are avoided. Indeed, spark creation with a laser becomes easier as cylinder pressure and density increase because at optical frequencies the required intensity to spark reduces with pressure, whereas the trend is opposite for conventional spark plugs since for conventional spark plugs the required electric field to spark increases with pressure.

Furthermore, by applying certain coatings to the inner wall of the hollow fiber the efficiency of light guiding can be increased, even in bent configurations. By doing so, the flexible coated hollow core fiber is able to deliver laser pulses to form sparks. In accordance with embodiments of the present invention, a system for generating a spark is provided, wherein the system comprises a laser beam and launch focusing optic or optics for receiving the laser beam, wherein the launch focusing optic or optics yield a focused beam of laser light at the entrance of the fiber. As used herein, both of the terms "optic" and "optics" refer to one or more devices for altering a beam of light, as for example, a single lens (simple or compound), a (curved) mirror, an active or adaptive optic, a diffractive optic, or a plurality of the aforementioned components.

In one embodiment of the invention, the launch focusing optics comprises at least one lens or curved mirror (or other appropriate optic). The system for generating a spark also includes a laser transmission fiber comprising a hollow bore and a wall surrounding the hollow bore (i.e., a hollow fiber), wherein the laser transmission fiber receives the focused beam of laser light at a fiber entrance. The laser transmission fiber transmits the beam of laser light through the fiber, and the beam of laser light exits the laser transmission fiber at a fiber exit as an exit beam of laser light. The system also includes exit focusing optics for receiving the exit beam of laser light from the fiber exit. In one embodiment of the invention, the exit focusing optics comprises at least one lens (or curved mirror or other appropriate optic), or alternatively, a plurality of lenses (or curved mirrors or other optic combinations). The exit focusing optics yields a focused beam capable of generating a spark.

In accordance with yet other embodiments of the present invention, a spark generating system is provided in combination with a combustion engine. In particular, the spark generation system is used to introduce a focused beam of laser light into a combustion chamber of the engine, thereby generating a spark within the combustion engine. In accordance with embodiments of the present invention, a multiplexer may be used with a single laser source and a plurality of hollow fibers for generating sparks at a plurality of spark targets, such as plurality of cylinders within a single combustion engine.

In accordance with embodiments of the present invention, sparking at the launch or at other locations within the fiber is at least partially alleviated by introducing (or flowing) a gas with high ionization potential (e.g., helium) or by using a vacuum set-up to lower the gas pressure at the launch and/or within the fiber. Both methods increase the breakdown threshold and thus help avoid sparking.

In accordance with other embodiments of the present invention, a method of generating a spark is provided. In general, the method involves using the spark generating system described above. More particularly, the method comprises providing a laser light source for generating a laser beam and providing launch optics for receiving the laser beam, wherein the launch optics yield a focused beam of laser light at the entrance of the fiber. The method also includes providing a laser transmission fiber comprising a hollow bore and a wall surrounding the hollow bore. The laser transmission fiber receives the focused beam of laser light at the fiber entrance. The laser transmission fiber transmits the focused beam of laser light through the fiber, and the beam of laser light exits the hollow fiber at a fiber exit as an exit beam. The method also includes aligning the launch lens with the fiber entrance of the laser transmission fiber. The method also includes providing exit optics in optical communication with the fiber exit, wherein the exit optics receives the exit beam of laser light from the fiber exit, and wherein the exit optics yields a focused beam for generating a spark. In addition, the method comprises generating a laser beam from the laser light source, wherein the laser beam generates the spark. The method may be used with a combustion engine, wherein the exit optics are operatively associated with a spark plug interconnected to a combustion engine.

In accordance with yet other embodiments of the present invention, a method of choosing a fiber for creating a spark using a laser beam is provided. The method generally includes assessing the intensity and the exit angle with which a beam of laser light exits a fiber of interest. These values are then entered into an equation, with the resultant of that equation for that particular type of fiber compared to a minimum value that is required for a fiber in general to be adequate for transmitting a laser beam and creating a spark. More particularly, after determining an exit intensity and an exit angle of a laser beam for a subject fiber, the method comprises calculating a "figure of merit" for the subject fiber and comparing the figure of merit for the subject fiber to a figure of merit minimum value for creating a spark. If the figure of merit for the subject fiber is high enough as compared to the figure of merit minimum value for creating a spark, then the subject fiber is suitable for use within system for generating a spark. If not, then it is not adequate for creating a spark, and either (1) other fibers should be considered, or (2) attempts can be made to adjust the launch lens and/or launch beam (and thus the launch angle and/or beam intensity profile of the laser beam entering the subject fiber), which then results in a potentially improved combination of exit angle and exit intensity, after which the figure of merit for the subject fiber can be recalculated and the comparison repeated.

Various embodiments of the present invention are set forth in the attached figures and in the detailed description of the invention as provided herein and as embodied by the claims. It should be understood, however, that this Summary of the Invention may not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

The drawings are not necessarily to scale.

DETAILED DESCRIPTION OF THE INVENTION

Figure 1:
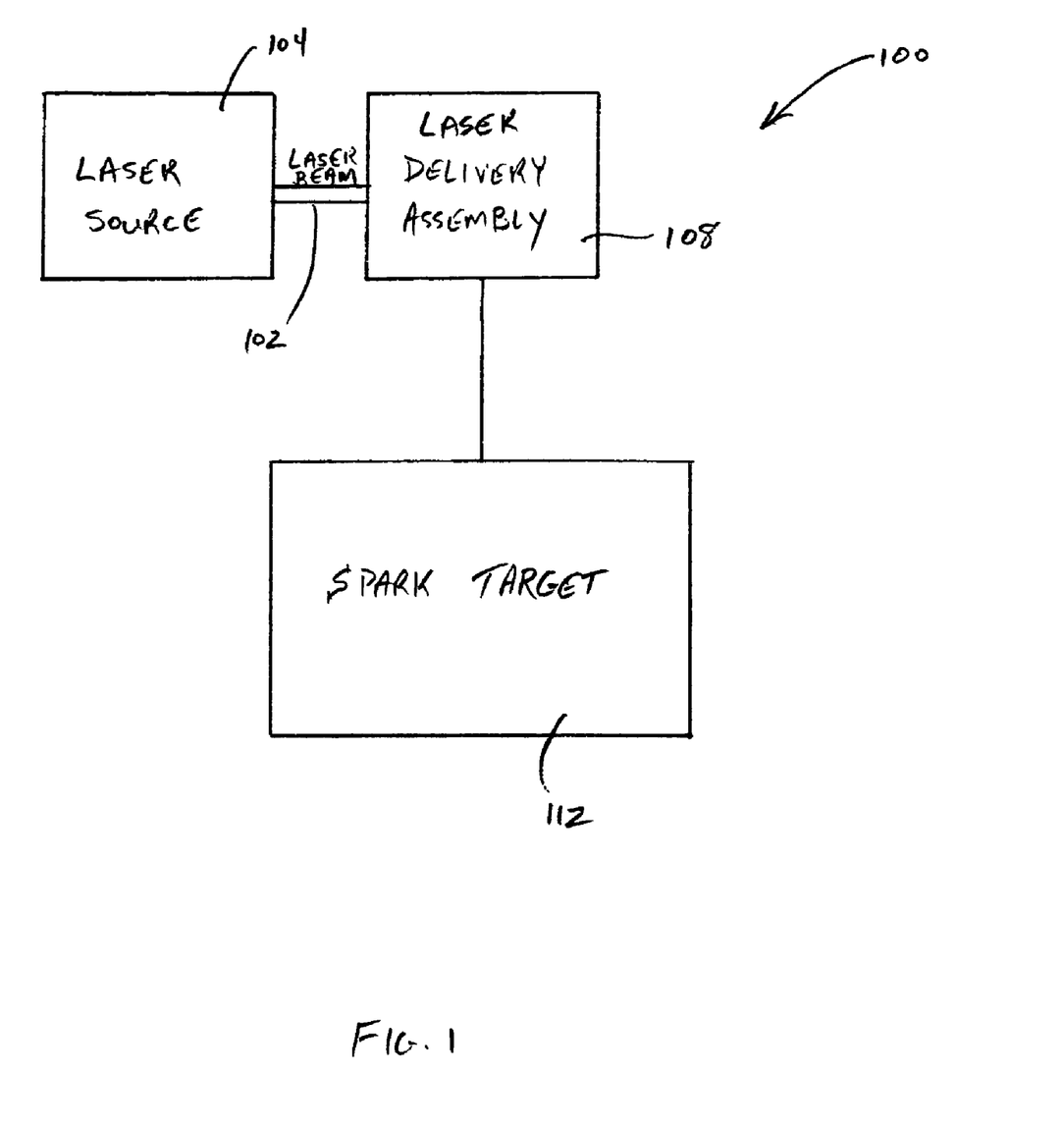
FIG. 1 is block diagram depicting components of a system in accordance with embodiments of the present invention.

FIG. 1 illustrates a spark delivery system 100 in accordance with embodiments of the present invention. The system 100 generally includes a laser source 104 in optical communication with a laser delivery assembly 108, which in turn is in optical communication with a spark target 112. The laser source 104 provides a beam of laser light 102 to the laser delivery assembly 108. In order to provide a desirable launch, a laser source 104 with a relatively high spatial quality is desirable. It is estimated that a laser source 104 with a spatial quality $M^2$ parameter of less than about 10 is required. In accordance with embodiments of the present invention, and by way of example and not limitation, a laser source 104 such as a Continuum 8000 Nd:YAG laser has been found to provide an acceptable laser beam 102 for sparking. In accordance with embodiments of the present invention, and by way of example and not limitation, a wavelength of 1064 nm has been found sufficient for sparking; however, many wavelengths of light are anticipated to work and are within the scope of the present invention. The laser delivery assembly 108 manipulates and conveys the laser light beam to the spark target 112. The spark target 112 can be a variety of devices or structures, such as, but not limited to, a combustion engine or another device or location requiring an ignition source or spark delivery. For the case of a combustion engine, the spark is formed within the gaseous region inside the combustion chamber or engine cylinder.

Figure 2:
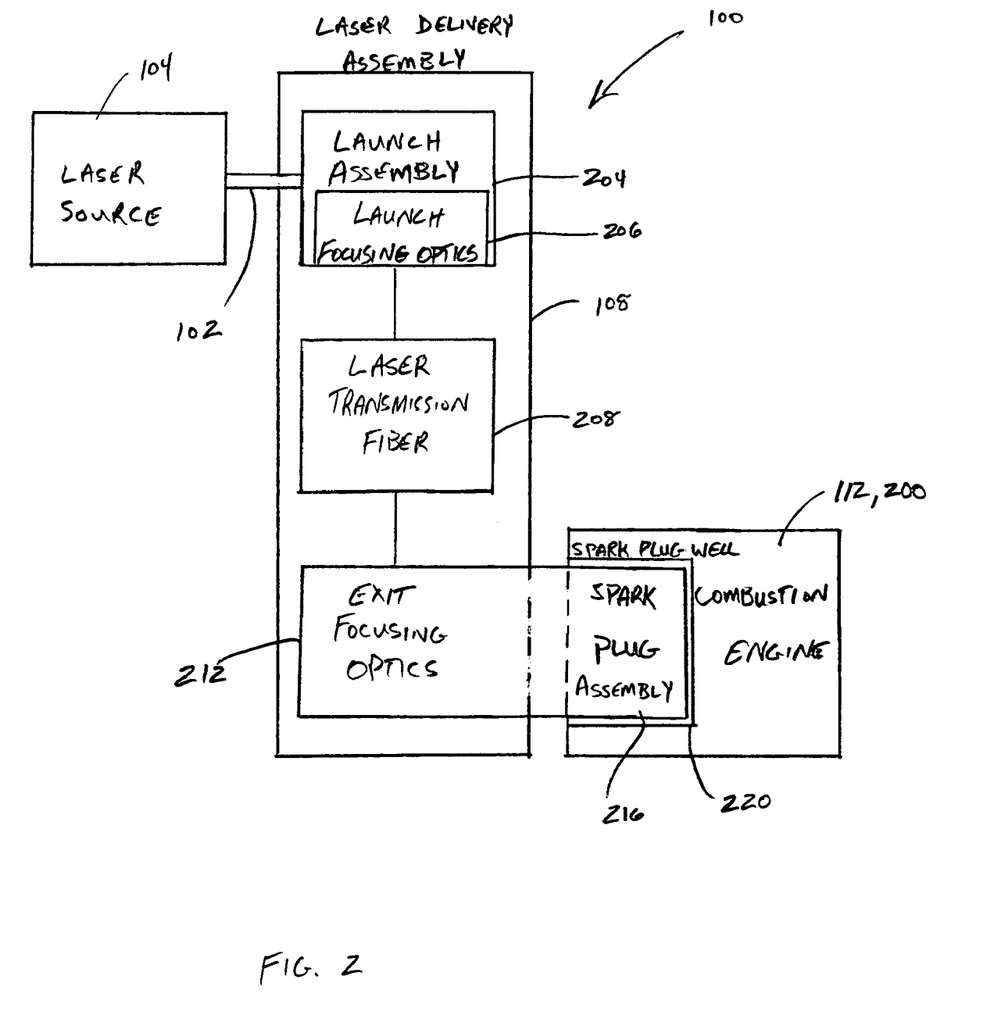
FIG. 2 is a block diagram depicting a combustion engine used in accordance with embodiments of the present invention.

Referring now to FIG. 2, a spark delivery system 100 is illustrated in accordance with an embodiment of the present invention, wherein the system 100 includes a spark target 112 comprising a combustion engine 200. FIG. 2 further illustrates that the laser delivery assembly 108 includes a launch assembly 204 that comprises launch focusing optics 206. In addition, the laser delivery assembly 108 includes a laser transmission fiber 208, and exit focusing optics 212. The exit focusing optics 212 are in optical communication with an optical spark plug assembly 216, which is interconnected to the combustion engine 200. By way of example and not limitation, the spark plug assembly 216 may contain at least a portion of the exit focusing optics. In addition, at least a portion of the spark plug assembly 216 may be inserted into a spark plug well 220 of the combustion engine 200.

Figures 3, 4, 5:
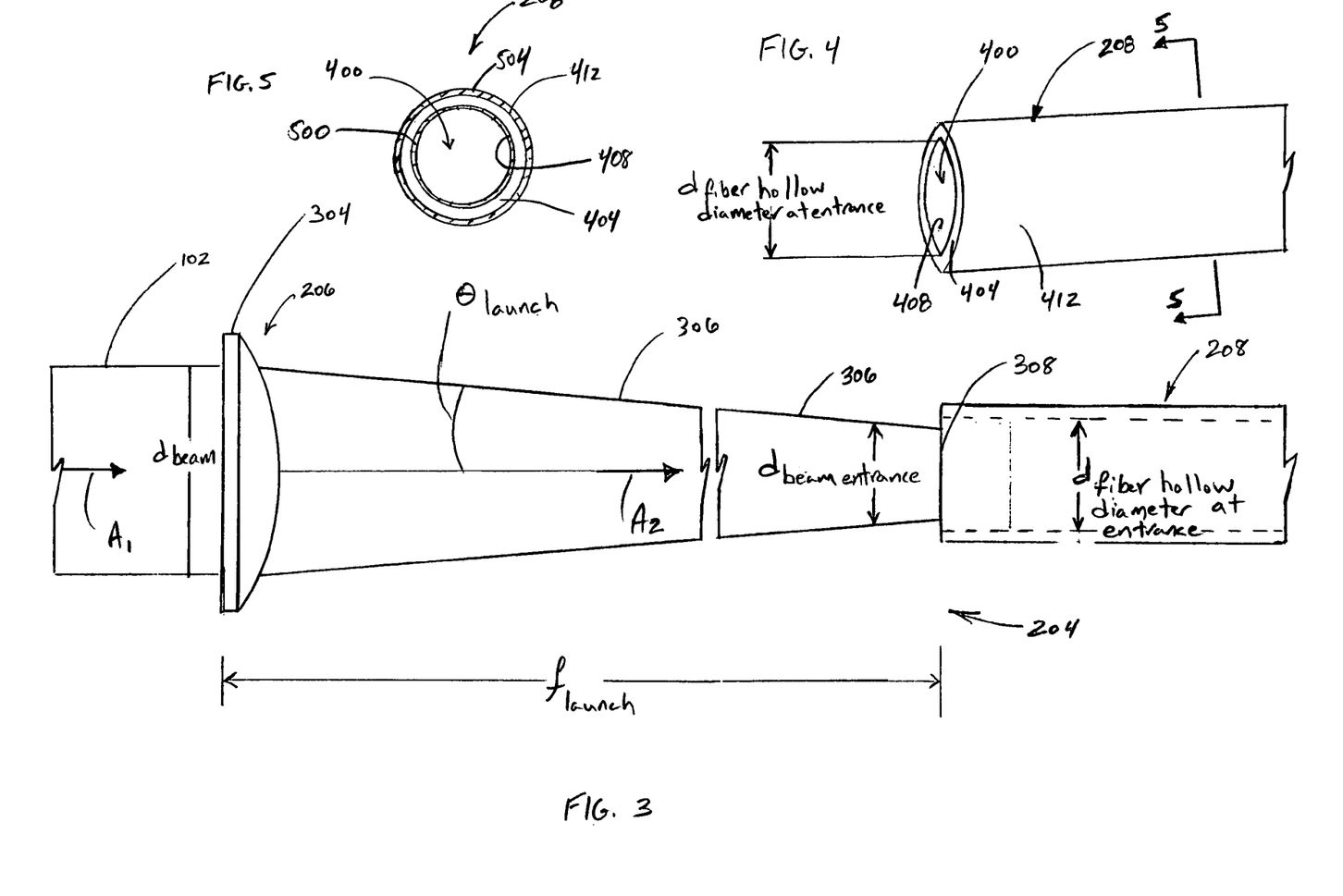
FIG. 3 is a side elevation view of the launch assembly in accordance with embodiments of the present invention.
FIG. 4 is a perspective view of a laser transmission fiber in accordance with embodiments of the present invention.
FIG. 5 is cross-sectional view of the laser transmission fiber of FIG. 4 taken along line 5-5 of FIG. 4.

Referring now to FIG. 3, in accordance with embodiments of the present invention, aspects of the launch assembly 204 are illustrated. The launch assembly 204 includes launch focusing optics 206 that receive the laser beam 102 generated by the laser source 104. In accordance with embodiments of the present invention, and by way of example and not limitation, as shown in FIG. 3, the launch focusing optics 206 may comprise a single launch lens 304, such as a plano-convex lens of 50 cm focal length; however, other lenses (simple or compound) and focal lengths, other optics (such as (curved) mirrors, as well as diffractive optics, and active or adaptive optics, and/or other appropriate optics) are within the scope of the present invention. Moreover, it can be appreciated and is to be understood that the launch focusing optics 206 (and exit optics as described below) may alternatively comprise a plurality of optical components, such as lenses, (curved) mirrors, diffractive optics, active or adaptive optics, and other appropriate optics and combinations of the aforementioned, etc. Indeed, it is anticipated that a variety of possible types of lens or lens systems are appropriate for use in the present invention, where the lens or lens systems may differ in material, shape and number. Thus, the focusing optics and exit optics may comprise mirrors and/or other devices different than a lens or lens system. In addition, the use of adaptive optics is disclosed in U.S. Pat. No. 6,796,278, which is incorporated herein by reference in its entirety. The use of all of such available devices are within the scope of the present invention.

Referring still to FIG. 3, for clarity, the beam contours are represented with straight lines, though in fact, they may have a slight curvature. In accordance with embodiments of the present invention, the focusing optics 206 or launch lens 304 demagnifies and focuses the light to launch the laser beam 102 into the laser transmission fiber 208. However, it is to be understood that alternate embodiments may comprise magnification optics depending upon the size of the laser beam diameter and the size of the fiber. By way of example and without limitation, for a launch using a single lens and a relatively collimated laser beam, the distance between the launch lens 304 and the fiber entrance 308 of the laser transmission fiber 208 is approximately the lens focal length $f_{launch}$. The launch lens 304 receives a laser beam 102 entering the launch lens 304 in the direction of arrow $A_1$. By way of example and not limitation, in an embodiment of the present invention the laser beam 102 has a beam diameter $d_{beam}$ of about 1 cm. By way of example and not limitation, in an embodiment of the present invention, the launch lens 304 demagnifies and focuses the laser beam 102 with a focal length $f_{launch}$ of about 50 cm as it enters the laser transmission fiber 208 in the direction of arrow $A_2$. For these conditions, the launch angle $\theta_{launch}$ of the focused laser light 306 is about 0.01 radians, yielding an exit angle $\theta_{exit}$ of light of approximately 0.01 to 0.02 radians. More generally, the launch angle should preferably be less than about 0.03 radians, and more preferably, less than about 0.015 radians, and the light exiting the fiber should have an exit angle $\theta_{exit}$ of less than about 0.03 radians, and more preferably, less than about 0.015 radians exiting the laser transmission fiber 208 near the exit focusing optics 212 (see FIG. 6). As will be appreciated by those skilled in the art, the beam intensity of a laser beam is generally not spatially uniform. Thus, there are different ways to define the beam diameter. As used herein, we define the beam diameter as four times the standard-deviation of the intensity profile. Equivalently, we define the diameter as twice the beam spot-size, where the spot-size is defined as twice the standard-deviation (where the standard-deviation is the square-root of the variance of the spatial intensity profile). Both the launch angle $\theta_{launch}$ and the exit angle $\theta_{exit}$ of light represent the angles between light rays corresponding to the beam diameter and the optical center axis at the respective component. For the case of a uniform beam profile, the angles $\theta_{launch}$ and $\theta_{exit}$ correspond to the half-angle of the widest rays of the beam.

Referring now to FIGS. 3 and 4, a laser transmission fiber 208 in accordance with an embodiment of the present invention is illustrated. The laser transmission fiber 208 comprises an optic fiber having a hollow bore 400 and a wall 404 circumscribing and surrounding the hollow bore 400. The wall 404 surrounding the hollow bore 400 has an interior wall surface 408. In addition, the wall 404 comprises an exterior wall surface 412. In order to be practically useful, the laser transmission fiber is preferably flexible, with a variety of possible radii of curvature. More particularly, a flexible fiber is preferred, and it is anticipated that a fiber having a radius of curvature of greater than at least about 1 to 10 cm is functional; that is, a variety of curvatures are possible from nearly straight fibers with an infinite or nearly infinite radius of curvature, to fibers having a radius of curvature as low as about 1 to 10 cm.

As noted above, in one embodiment of the present invention the laser beam 102 entering the launch lens 304 has a beam diameter $d_{beam}$ of about 1 cm. As the launch angle $\theta_{launch}$ is decreased, the diameter of the beam at the fiber entrance 308 increases. However, it is necessary for the diameter of the beam $d_{beam\ entrance}$ at the fiber entrance 308 to be less than the diameter $d_{fiber\ hollow\ diameter\ at\ entrance}$ of the hollow bore of the fiber 208 at the fiber entrance 308 in order to prevent sparking at the fiber face (which may occur if the edge of the beam overlaps the fiber wall), and to transfer sufficient beam energy to the fiber 208.

In addition, if the diameter of the beam $d_{beam\ entrance}$ at the fiber entrance 308 becomes too small, the corresponding intensity will become sufficiently high to cause sparking of the ambient gas at the fiber entrance 308. Accordingly, the diameter of the beam $d_{beam\ entrance}$ at the fiber entrance 308 should be not so small that the intensity at the fiber entrance reaches the breakdown intensity and causes a spark at the fiber entrance. In practice, this will generally, but not necessarily, require a diameter between about 10 and 90% of the outside diameter $d_{fiber\ hollow\ diameter\ at\ entrance}$ of the fiber 208 at the fiber entrance 308. By way of example and not limitation, in one embodiment of the invention, the diameter of the beam $d_{beam\ entrance}$ at the fiber entrance 308 is about 300 microns for a fiber 208 having a diameter $d_{fiber\ hollow\ diameter\ at\ entrance}$ of about 700 microns at the fiber entrance 308. In addition, in accordance with embodiments of the present invention, sparking at the fiber entrance 308 or at other locations within the fiber is at least partially alleviated by introducing (or flowing) a gas with high ionization potential (e.g., helium) or by using a vacuum set-up to lower the gas pressure at the launch and/or within the fiber. Both methods increase the breakdown threshold and thus help avoid sparking.

In accordance with embodiments of the present invention, five axes of control are needed to correctly align the fiber 208 with the focused laser light 306, assuming that the light beam is fixed, and that the fiber is aligned with the beam. The axes comprise the three spatial axes (i.e., the position of the fiber input) as well as two tilt axes. Spatially, the x axis (where the x-axis is defined by a line joining the center of the launch lens with the center of the fiber input face) is the least critical, requiring placement of the fiber entrance within a few millimeters of the launch beam waist along the beam's axial direction. However, both the spatial y and z axes and the two tilt axes must be carefully aligned (on the order of 10's of microns and milli radians for the example parameter values given above) to get efficient transmission through the fiber and to avoid exciting higher order modes and thereby further decreasing the spatial quality (increasing $M^2$) of the beam through the fiber 208. It is also noted that it would be possible to perform a combination of aligning the beam to the fiber and the fiber to the beam, in which case less than five axes would be needed for the fiber adjustment since one or more axes could be done with laser adjustment.

Referring now to FIG. 5, a cross section of a transmission fiber in accordance with at least one embodiment of the invention is shown. The interior wall surface 408 is coated with an interior coating 500, and the exterior wall surface 412 is coated with an exterior coating 504. The coating 500 may be formed of a single or multiple number of layers, or may be integral to the wall material. The coating 504 may be formed of a single or multiple number of layers. Alternatively, in one embodiment, the exterior coating 504 may be absent. In addition, the coatings may be formed from metal and/or other materials (e.g., polymers). Typically, the layer thicknesses must be tightly controlled, generally as a function of the laser wavelength, to allow for effective light guiding. By way of example and not limitation, in one embodiment of the invention, the coating 500 is comprised of a layer of silver of approximately 0.2 microns in thickness, which is on the inner wall surface 408, and a cyclic olefin polymer coating (placed on the silver coating) of approximately 0.1 microns in thicknesses.

Figure 6:
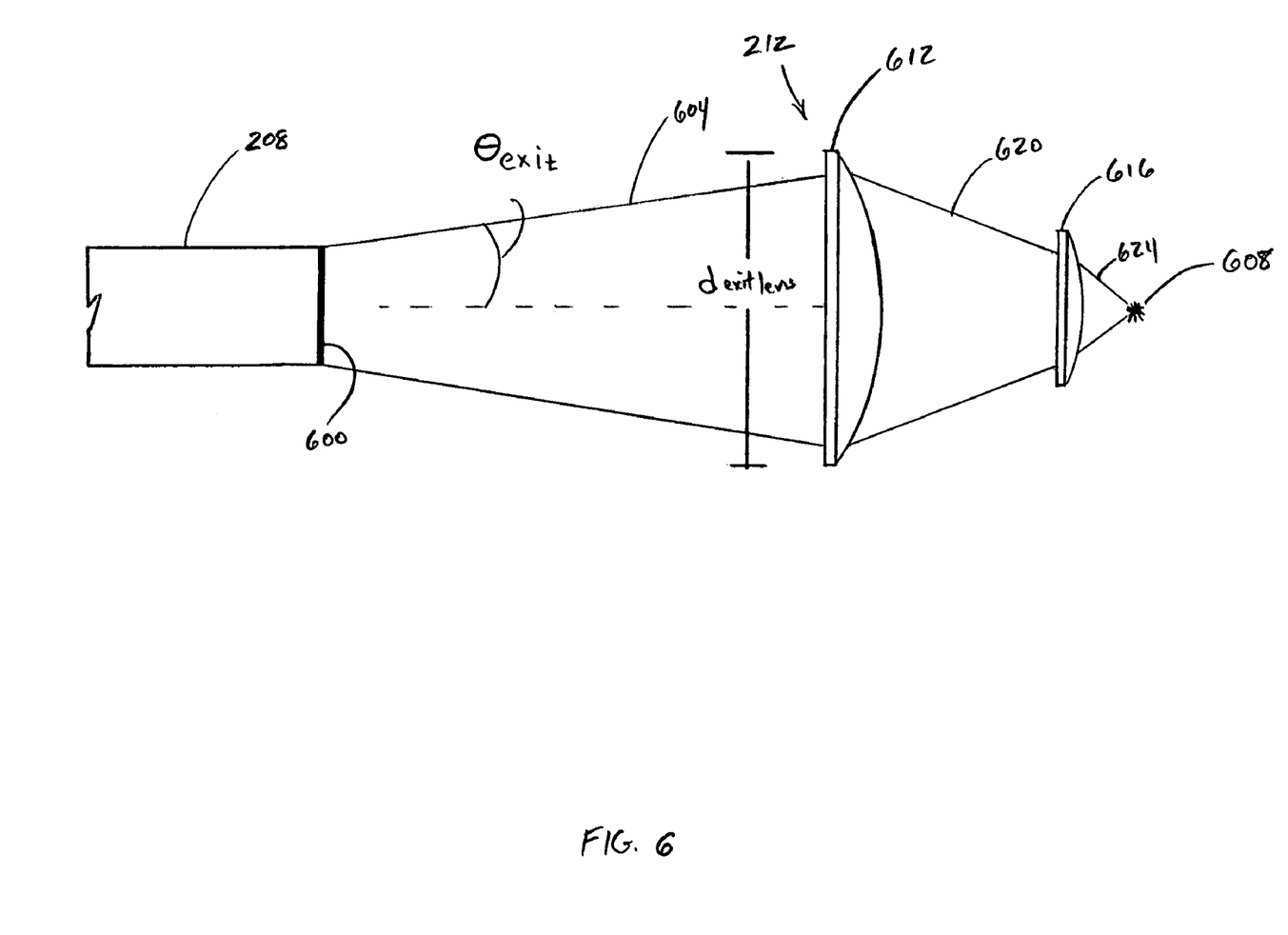
FIG. 6 is a side elevation view of the fiber exit and exit focusing optics in accordance with embodiments of the present invention.

Referring now to FIG. 6, in accordance with embodiments of the present invention, the fiber exit 600 and exit focusing optics 212 are shown. Light traveling through the fiber 208 exits the fiber at an exit angle $\theta_{exit}$ at the fiber exit 600. For clarity, the beam contours are represented with straight lines, though in fact, they may have a slight curvature. The exit beam 604 is directed toward the exit focusing optics 212, in which the beam 604 is demagnified to create a spark 608.

In accordance with embodiments of the present invention, the exit focusing optics 212 are selected to allow small focal spots at the desired spark location, thus providing high demagnification of light exiting the fiber, and thereby providing high intensities at the desired spark location. Since the exit beam 604 exiting the fiber 208 is not collimated, the separation distance of the exit focusing optics 212 from the fiber exit 600 is important. An effective configuration comprises a low f# ("f number") optic system; that is, a low ratio of effective focal length to lens fill diameter, and is positioned downstream from the fiber exit 600 in such a way that the exit beam 604 does not exceed the exit lens diameter $d_{exit\ lens}$ (i.e., the beam should not overfill the lens). A low f# system is required as it is capable of focusing the light leaving the fiber to a small beam diameter to achieve the required high intensity. As shown in FIG. 6, and by way of example and without limitation, at least one embodiment of the present invention employs two exit lenses 612 and 616 with a resulting demagnification ratio of the light dimension leaving the fiber to the light dimension at the spot of the spark 608 of about 10. The exit lenses 612 and 616 demagnify the exit beam 604 to create focused beams 620 and 624, thereby providing the intensity required to produce the spark 608.

The practical limitation on low f# optics which give high demagnification, is that aberrations tend to become increasingly prevalent as the f# is reduced. Since aberrations cause larger spot sizes and thus are undesirable because they decrease the intensity of the beam at the spark location, an imaging system with simultaneous low f# and low aberrations is preferable. In accordance with embodiments of the present invention, the exit focusing optics 212 allow appropriate demagnification and refocusing. By way of example and without limitation, the exit focusing optics 212 may be based on a single- or multi-lens system, and may use simple spherical lenses, plano-spherical lenses, achromatic lenses, or aspheric lenses. Alternatively, the exit optics 212 may comprise other optics, either with or without the use of one or more lenses, such as one or more curved mirrors, diffractive optics, and/or active or adaptive optics, allowing appropriate demagnification and refocusing.

The exit focusing optics 212 allow the spark 608 to be positioned at a desired location. For example, when used in a combustion engine 200, the exit optics 212 may be designed to provide demagnification of the exit beam 604 such that the spark 608 is generated at an optimum location. More particularly, by adjusting the exit optics 212, the spark 608 may be moved away from the relatively cold combustion chamber walls, thus removing the walls as a "heat sink" that can slow down early flame growth in an engine. As discussed earlier, there may be other benefits associated with moving the spark location.

In accordance with other embodiments of the invention, a method of generating a spark using a spark delivery system 100 as described herein is provided. In use, a laser source 104 is provided and a laser beam 102 is directed to a laser delivery assembly 108. The laser beam 102 is received by launch focusing optics 206 that typically comprises at least one launch lens 304, but may be comprised of other devices, such as a mirror. The focused laser light 306 from the launch lens 304 is directed to a fiber entrance 308 of a laser transmission fiber 208 that comprises a coated hollow core fiber that is preferably flexible. The process of directing the laser light 306 from the launch lens 304 to the fiber entrance 308 typically entails aligning the light 306 along five axes of control, including three spatial axes and two tilt axes. After the light passes through the fiber 208 and exits the fiber 208 at a second end or fiber exit 600 of the fiber 208, the exit beam 604 is then directed to exit focusing optics 212 which may comprise one or more lenses, such as exit lenses 612 and 616. The exit focusing optics 212 cause an increase in intensity of the exit beam 604, creating an electrical breakdown at the location of the spark target 112, thereby creating a spark 608. For use in a combustion engine 200, the exit focusing optics 212 are interconnected to a spark plug assembly 216 that is interconnected to the combustion engine 200, such as through a spark plug well 220. When the spark 608 is created in an ignitable gas, the spark causes ignition within the engine 200.

Figure 8:
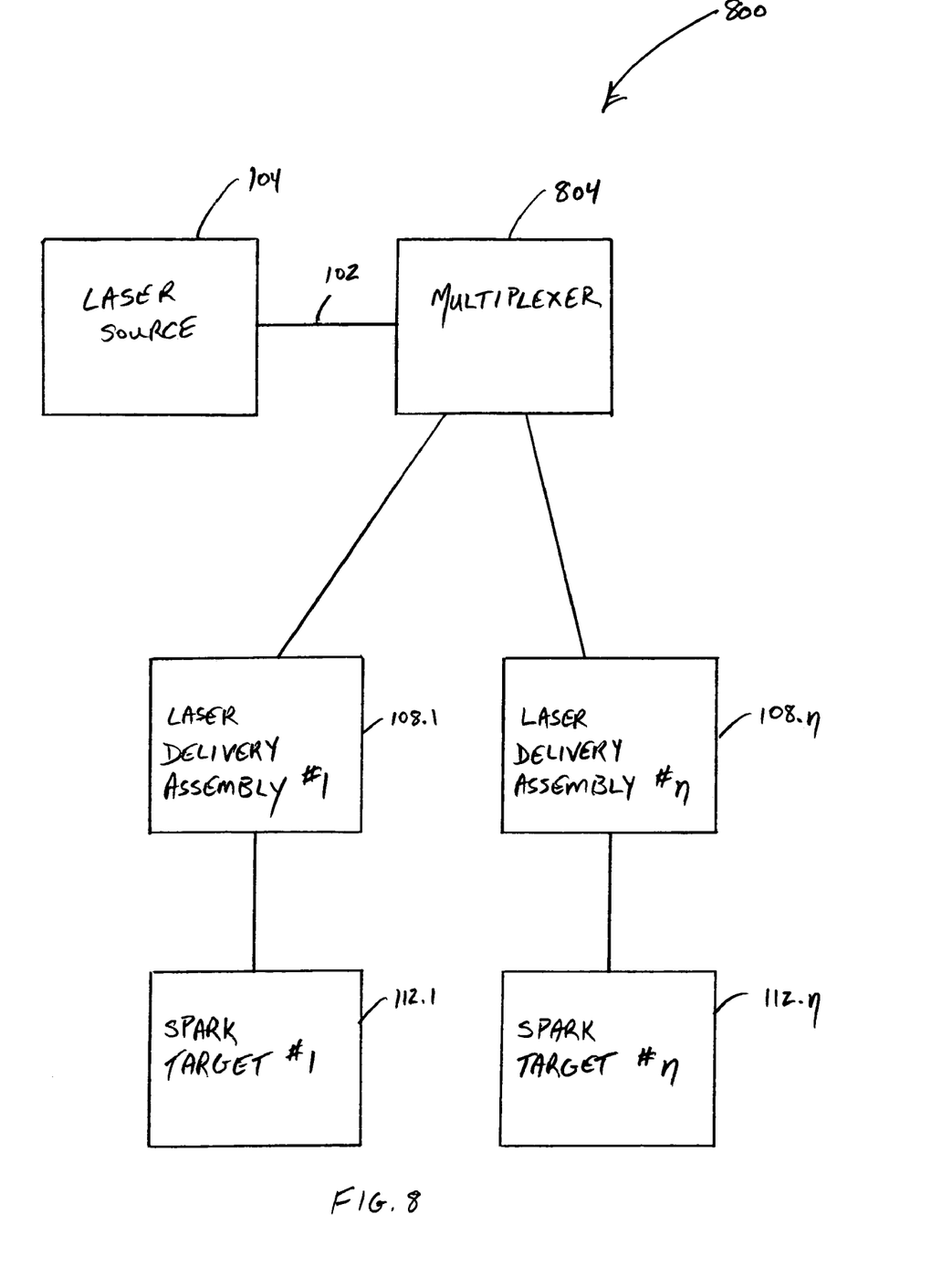
FIG. 8 is a block diagram depicting a multiplexed spark delivery system in accordance with embodiments of the present invention.

Referring now to FIG. 8, in accordance with embodiments of the present invention, a multiplexed spark delivery system 800 can be used, wherein a single laser source is used to provide a laser beam to a plurality of hollow fibers. As shown in FIG. 8, a multiplexer 804 is positioned between the laser source 104 and a plurality of laser delivery assemblies 108.1-108.$n$, wherein the laser delivery assemblies 108.1-108.$n$ deliver a focused laser beam to spark targets 112.1-112.$n$, respectively. By way of example and without limitation, a multiplexed spark delivery system 800 can be used with a combustion engine, wherein a single laser source is used to provide a laser beam through a plurality of hollow fibers leading to multiple cylinders within a single combustion engine.

The laser spark delivery system of the present invention may have applications in other areas, as for example, for spark delivery in laser induced breakdown spectroscopy (LIBS) diagnostics or for medical or dental applications. Accordingly, the present invention disclosure encompasses the use of optical spark delivery in any appropriate application, not just for ignition.

In a separate embodiment of the invention, a method of choosing a fiber for creating an optical spark is provided. The method involves calculating a figure of merit ("FOM") to compare the different types of fibers, as well as fiber lasers, in terms of their effectiveness for creating optical sparks. The figure of merit was derived from the point of view of paraxial ray-tracing (geometric optics), and may also be derived from spatial beam quality ($M^2$) considerations. Both analyses are equivalent under certain simplifying assumptions, namely, that the light exiting the fiber has a waist (minimum spot-size) equal to the fiber radius and that the far-field beam divergence matches the fiber exit angle.

Figure 7:
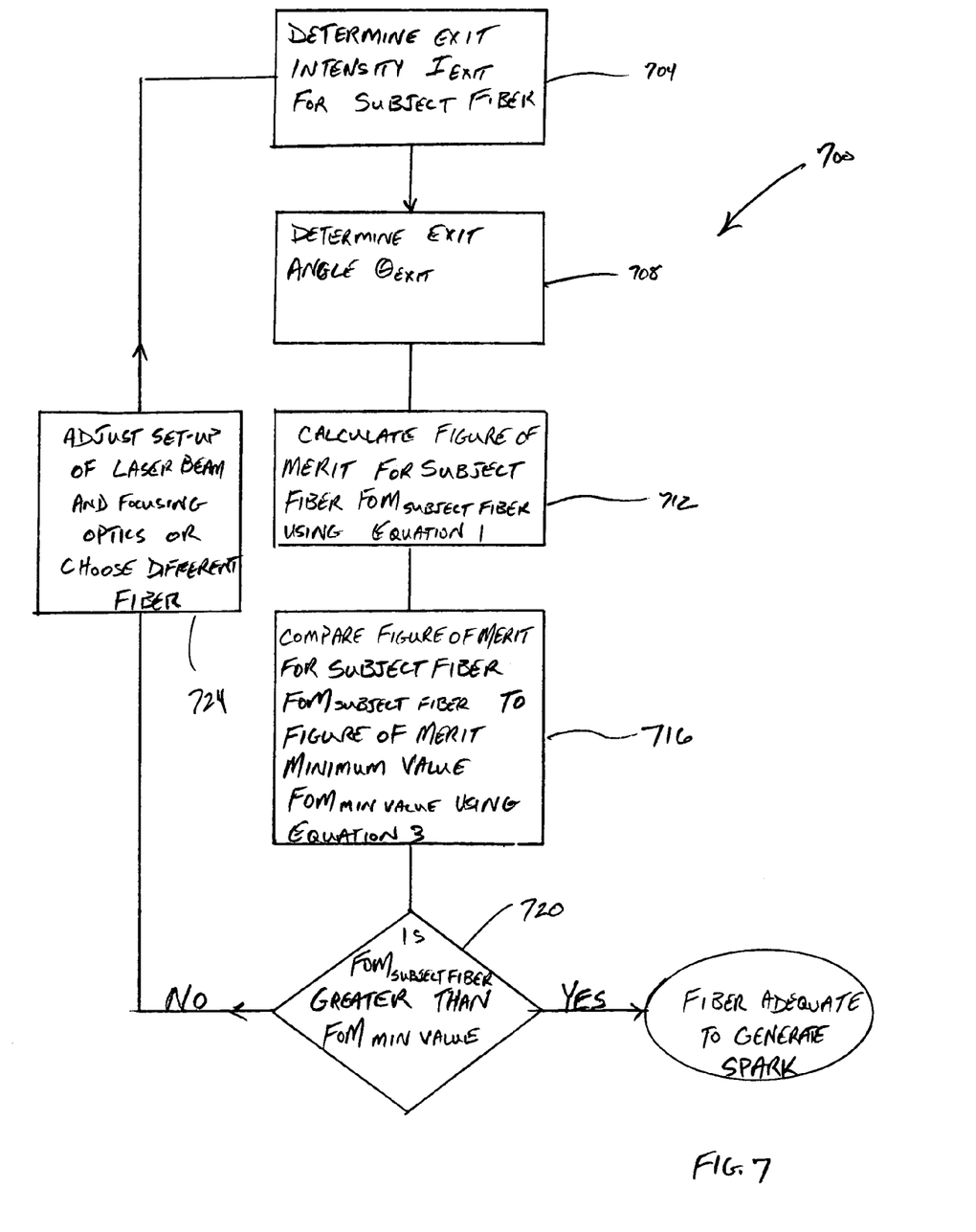
FIG. 7 is a flow diagram depicting aspects of a method of choosing a fiber to create a spark using a laser in accordance with embodiments of the present invention.

With reference now to FIG. 7, a method of choosing a fiber for creating an optical spark in accordance with an embodiment of the present invention is illustrated in a flow diagram. The method applies to a single lens and a multi-lens imaging system. The method of choosing a fiber includes calculating a figure of merit "FOM" for the subject fiber $FOM_{subject\ fiber}$, and comparing this value to a calculated figure of merit minimum value $FOM_{min\ value}$ for creating a spark. For ease of analysis, it is assumed that the light at the fiber exit uniformly fills the fiber diameter, and that the final focusing optics have negligible transmission loss. More specifically, the intensity should be considered as the spatially and temporally averaged intensity.

The figure of merit for the subject fiber:

$$FOM_{subject\ fiber} = \frac{I_{exit}}{\theta_{exit}^2} \quad \text{[Equation 1]}$$

and intensity at the spark location is given as:

$$I_{spark} = \frac{I_{exit} \theta_{spark}^2}{\theta_{exit}^2} \quad \text{[Equation 1.5]}$$

Thus, the figure of merit minimum value for creating a spark is given as:

$$FOM_{min\ value} = \frac{I_{spark}}{\theta_{spark}^2} \quad \text{[Equation 2]}$$

where $I_{spark}$ is the minimum intensity value required to create a spark.

For these equations, the figure of merit is independent of the focusing optics. Assuming the required intensity at the spark location is $2\pm1\times10^{11}$ W/cm$^2$, and that the best achievable imaging is $\theta_{spark}=0.38\pm0.13$ radians (which corresponds to 0.5 to 0.25 radians, or equivalently a minimum imaging f#=1 to 2, then the minimum value $FOM_{min\ value}$ for creating a spark is:

$$FOM_{min\ value} \geq 1400\pm800\ GW/cm^2/rad^2 \quad \text{[Equation 3]}$$

The uncertainty in the $FOM_{min}$ is due to uncertainty in both the required intensity to spark ($I_{spark}$), and in the maximum possible divergence angle ($\theta_{spark}$) at the spark location, corresponding to minimum possible imaging f#. For example, if higher intensities are required to spark, the $FOM_{min}$ will increase as given by Equation 2, and the same logic applies to variation in $\theta_{spark}$.

The figure of merit for the subject fiber $FOM_{subject\ fiber}$ clearly shows that to achieve a high intensity at the intended spark location requires a high intensity ($I_{exit}$) at the fiber exit, as well as a low divergence angle or exit angle $\theta_{exit}$ at the fiber exit. This method may be used to compare the ease with which different sources (i.e. fiber types) can be focused to high intensity to produce sparks.

By way of example, a comparison is provided in Table 1 to compare different sources, and to gage the effectiveness of a given source for creating sparks, the FOM may be evaluated for different available solid and hollow core fiber optics. Results are given in Table 1 below. In Table 1, solid fiber refers to standard (commercial) silica step-index fibers of numerical aperture (NA) of 0.11.

TABLE 1

| Source | $I_{exit}$ (GW/cm$^2$) | $\theta_{exit}$ (Rad) | $FOM_{subject\ fiber}$ [Equation 1] (GW/cm$^2$/rad$^2$) |
|---|---|---|---|
| Solid Fiber (base NA) | ~3 | ~0.11 | ~250 |
| Solid Fiber (lower NA) | ~3 | ~0.05 | ~1200 |
| Coated Hollow Fiber | ~2 | ~0.015 | ~8900 |

With regard to the data presented in Table 1, the exit intensities $I_{exit}$ for the fibers are believed to be the highest reported for nanosecond lasers. Solid fibers are generally characterized by their Numerical Aperture (NA) which is defined by fiber index of refraction and generally corresponds also to the exit angle $\theta_{exit}$. The exit angles $\theta_{exit}$ for the Solid Fiber (base NA) is defined by an NA=0.11, which is typical for solid fibers. (Lower NA fibers are available in some cases but are generally less robust). Using the present method, the figure of merit for the subject fiber $FOM_{subject\ fiber}$ yields a value of approximately 250 GW/cm$^2$/rad$^2$ for the Solid Fiber (operated at base NA). This value is significantly lower than the minimum value $FOM_{min\ value}$ for creating a spark. Therefore, the present method rules out use of the Solid Fiber (base NA) for creating a spark.

The second row of Table 1 presents values for a solid fiber that operates with a lower exit angle (NA), which can be achieved by modifying the light delivery at the fiber entrance. The exit angle $\theta_{exit}$ value of 0.05 radians corresponds approximately to half the standard NA. Again, using the present method, the figure of merit for the subject fiber $FOM_{subject\ fiber}$ yields a value of approximately 1200 GW/cm$^2$/rad$^2$ for the Solid Fiber (lower NA). This value is in the range of the range for the minimum value $FOM_{min\ value}$ for creating a spark. Therefore, the present method indicates that use of the Solid Fiber (lower NA) may be possible for creating a spark. However, when operating at lower than base NA, the possible exit intensity tends to decrease, which causes a lowering of the $FOM_{subject\ fiber}$ for such implementations.

For the coated hollow fiber, the exit angle $\theta_{exit}$ value of 0.015 radians and the values of exit intensity are based on inferences from reported work and experiments. Using the present method, the figure of merit for the subject fiber $FOM_{subject\ fiber}$ yields a value of approximately 8900 GW/cm$^2$/rad$^2$ for the Coated Hollow Fiber. This value is greater than the range for the minimum value $FOM_{min\ value}$ for creating a spark. Therefore, the present method indicates that use of a Coated Hollow Fiber is acceptable for creating a spark.

With Reference again to FIG. 7, a method of choosing a laser transmission fiber 700 is provided. As shown in box 704, the method of choosing a fiber comprises determining the exit intensity $I_{exit}$ for a subject fiber. As shown in box 708, the method also includes determining the exit angle $\theta_{exit}$ of the widest rays of light exiting the subject fiber. In addition, as shown in box 712 the method includes calculating the figure of merit for the subject fiber $FOM_{subject\ fiber}$ using Equation 1. As shown in box 716, the method includes comparing the figure of merit for the subject fiber $FOM_{subject\ fiber}$ against the figure of merit minimum value $FOM_{min\ value}$ for creating a spark using Equation 3. As shown in box 720, if the calculated value for the figure of merit for the subject fiber $FOM_{subject\ fiber}$ of Equation 1 is less than the figure of merit minimum value $FOM_{min\ value}$ for creating a spark shown in Equation 3, the user of the method may attempt to adjust the launch conditions as shown in box 724. For example, the user can attempt to decrease the launch angle $\theta_{launch}$, thereby decreasing the exit angle $\theta_{exit}$, though associated changes in $I_{exit}$ must also be accounted for. Alternatively, the user may modify other conditions, such as the power of the laser beam in order to attempt to reach the minimum value $FOM_{min\ value}$ for creating a spark. If these modifications do not provide parameters yielding a sufficient figure of merit $FOM_{subject}$ fiber for the subject fiber, then the user can try a different type of fiber and repeat the process.

While various embodiments of the present invention have been described in detail, it is apparent that modifications and adaptations of those embodiments will occur to those skilled in the art. However, it is to be expressly understood that such modifications and adaptations are within the spirit and scope of the present invention.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for generating a spark, comprising:
   a laser light source, wherein said laser light source generates a laser beam;
   launch optics for receiving said laser beam, wherein said launch optics yields a first focused beam of laser light;
   a laser transmission fiber comprising a hollow bore and a wall surrounding said hollow bore, wherein said laser transmission fiber receives said first focused beam of laser light at a fiber entrance, wherein said laser transmission fiber transmits said first focused beam of laser light through said laser transmission fiber, and wherein said first focused beam of laser light exits said laser transmission fiber at a fiber exit as an exit beam of laser light; and
   exit optics for receiving said exit beam of laser light from said fiber exit, wherein said exit optics fields a second focused beam generating a spark.

2. The system as claimed in claim 1, wherein a beam diameter of said first focused beam of laser light at the fiber entrance is smaller than a diameter of said hollow bore of said laser transmission fiber, and wherein said first focused beam does not form a spark at the fiber entrance.

3. The system as claimed in claim 1, wherein said wall comprises an inside surface comprising a coating.

4. The system as claimed in claim 3, wherein said coating comprises a plurality of layers of material.

5. The system as claimed in claim 1, wherein said laser transmission fiber is flexible.

6. The system as claimed in claim 1, wherein said first focused beam of laser light has a launch angle of less than about 0.03 radians when entering said fiber entrance.

7. The system as claimed in claim 1, wherein said exit beam of laser light has an exit angle of less than about 0.03 radians when exiting said fiber exit.

8. The system as claimed in claim 1, wherein at least one of said launch optics and said exit optics comprises at least one lens.

9. The system as claimed in claim 1, wherein at least one of said launch optics and said exit optics comprises at least one curved mirror.

10. The system as claimed in claim 1, wherein at least one of said launch optics and said exit optics are selected from the group consisting of diffractive optics, active optics, adaptive optics, and a combination thereof.

11. The system as claimed in claim 1, wherein said laser transmission fiber comprises silica.

12. The system as claimed in claim 1, wherein said exit optics is operatively associated with a spark plug interconnected to a combustion engine.

13. The system as claimed in claim 12, wherein said spark plug is interconnected to the combustion engine at a spark plug well.

14. The system as claimed in claim 1, further comprising a multiplexer and at least a second laser transmission fiber.

15. A system for generating a spark, comprising:
   a means for generating a beam of laser light, said means for generating consisting essentially of a single laser light source that generates said beam of laser light;
   a means for focusing said beam of laser light, wherein said means for focusing provides a first focused beam of laser light;
   a laser transmission fiber comprising a hollow bore and a wall surrounding said hollow bore wherein the wall comprises an inside surface that comprises one or more of an interior layer and an interior coating, wherein said laser transmission fiber receives said first focused beam of laser light at a fiber entrance, wherein said laser transmission fiber transmits said first focused beam of laser light through said laser transmission fiber, and wherein said first focused beam of laser light exits said laser transmission fiber at a fiber exit as an exit beam of laser light; and
   a means for demagnifying said exit beam of laser light, wherein said means for demagnifying generates a spark from said exit beam of laser light.

16. The system as claimed in claim 15, wherein a beam diameter of said first focused beam of laser light at the fiber entrance is smaller than a diameter of said hollow bore of said laser transmission fiber, and wherein said first focused beam does not form a spark at the fiber entrance.

17. The system as claimed in claim 15, wherein said wall comprises an inside surface comprising a coating.

18. The system as claimed in claim 17, wherein said coating comprises a plurality of layers of material.

19. The system as claimed in claim 15, wherein said laser transmission fiber is flexible.

20. The system as claimed in claim 15, wherein said first focused beam of laser light has a launch angle of less than about 0.03 radians when entering said fiber entrance.

21. The system as claimed in claim 15, wherein said exit beam of laser light has an exit angle of less than about 0.03 radians when exiting said fiber exit.

22. The system as claimed in claim 15, wherein said laser transmission fiber comprises silica.

23. The system as claimed in claim 15, wherein at least one of said means for focusing and said means for demagnifying comprise at least one lens.

24. The system as claimed in claim 15, wherein at least one of said means for focusing and said means for demagnifying comprise at least one curved mirror.

25. The system as claimed in claim 15, wherein at least one of said means for focusing and said means for demagnifying are selected from the group consisting of diffractive optics, active optics, adaptive optics, and a combination thereof.

26. The system as claimed in claim 15, wherein said means for demagnifying is operatively associated with a spark plug interconnected to a combustion engine.

27. The system as claimed in claim 26, wherein said spark plug is interconnected to the combustion engine at a spark plug well.

28. The system as claimed in claim 15, further comprising a means for multiplexing the beam of laser light and at least a second laser transmission fiber.

29. A system for generating a spark, comprising:
a laser light source, wherein said laser light source consists essentially of a single laser light source that generates a laser beam;
launch optics for receiving said laser beam, wherein said launch optics yields a first focused beam of laser light;
a flexible laser transmission fiber comprising a hollow bore and a wall surrounding said hollow bore wherein the wall comprises an inside surface that comprises at least one of an interior layer and an interior coating, wherein said laser transmission fiber receives said first focused beam of laser light at a fiber entrance, said first focused beam of laser light has a launch angle of less than about 0.03 radians when entering said fiber entrance, wherein said laser transmission fiber transmits said first focused beam of laser light through said laser transmission fiber, and wherein said first focused beam of laser light exits said laser transmission fiber at a fiber exit as an exit beam of laser light, wherein said exit beam of laser light has an exit angle of less than about 0.03 radians when exiting said fiber exit; and
exit optics operatively associated with a spark plug interconnected to a combustion engine at a spark plug well, said exit optics for receiving said exit beam of laser light from said fiber exit, wherein said exit optics fields a second focused beam generating a spark sufficient for igniting a fuel and air mixture.

30. The system as claimed in claim 29, wherein at least one of said launch optics and said exit optics are selected from the group consisting of a lens, a plurality of lenses, a curved mirror, a plurality of curved mirrors, diffractive optics, active optics, adaptive optics, and a combination thereof.

31. The system as claimed in claim 29, further comprising a multiplexer and at least a second flexible laser transmission fiber.

32. A method of generating a spark, comprising:
providing a laser light source, wherein said laser light source consists essentially of a single laser light source for generating a laser beam;
providing launch optics for receiving the laser beam, wherein the launch optics fields a first focused beam of laser light;
providing a laser transmission fiber comprising a hollow bore and a wall surrounding the hollow bore wherein the wall comprises an inside surface that comprises one or more of an interior layer and an interior coating, wherein the laser transmission fiber receives the first focused beam of laser light at a fiber entrance, wherein the laser transmission fiber transmits the first focused beam of laser light through the laser transmission fiber, and wherein the first focused beam of laser light exits the hollow fiber at a fiber exit as an exit beam;
aligning the launch optics with the fiber entrance of the laser transmission fiber; and
generating the spark using exit optics in optical communication with the fiber exit, wherein the exit optics receives the exit beam of laser light from the fiber exit, and wherein the exit optics fields a second focused beam for generating the spark.

33. The method as claimed in claim 32, wherein said aligning comprises using a plurality of axes of control.

34. The method as claimed in claim 32, wherein said exit optics is operatively associated with a spark plug interconnected to a combustion engine.

35. The method as claimed in claim 32, further comprising directing the laser beam to a plurality of spark targets using a multiplexer.

36. The method as claimed in claim 32, further comprising at least partially purging ambient air at the fiber entrance.

37. The method as claimed in claim 32, further comprising at least partially purging ambient air at one or more of the fiber entrance and the hollow bore using a gas having a high ionization potential.

38. The method as claimed in claim 32, further comprising at least partially purging ambient air at one or more of the fiber entrance and the hollow bore by applying a vacuum.

39. A system for generating a spark in a combustion engine, the system including a laser light source, wherein said laser light source generates a beam of laser light, the system further comprising:
a hollow fiber for conveying the beam of laser light to exit optics, the hollow fiber including a hollow bore and a wall surrounding said hollow bore, wherein the wall comprises an inside surface that comprises one or more of an interior layer and an interior coating, the exit optics for demagnifying the beam of laser light and generating the spark in the combustion engine.

40. The system as claimed in claim 39, wherein said beam of laser light comprises a launch angle of less than about 0.03 radians when entering said hollow fiber.

41. The system as claimed in claim 39, wherein said laser beam comprises an exit angle of less than about 0.03 radians when exiting said hollow fiber.

42. The system as claimed in claim 39, wherein said exit optics comprises at least one of diffractive optics, active optics, adaptive optics, and a combination thereof.

* * * * *